(12) United States Patent
Luo

(10) Patent No.: US 11,389,527 B2
(45) Date of Patent: Jul. 19, 2022

(54) METHODS OF INDUCING AN IMMUNE RESPONSE AGAINST HIV-1 UTILIZING NUCLEIC ACIDS ENCODING POLYPEPTIDES CONTAINING HIV-1 PROTEASE CLEAVAGE SITES

(71) Applicant: Her Majesty the Queen in Right of Canada as Represented by the Minister of Health, Winnipeg (CA)

(72) Inventor: Ma Luo, Winnipeg (CA)

(73) Assignee: Her Majesty the Queen in Right of Canada as Represented by the Minister of Health, Winnipeg (CA)

( * ) Notice: Subject to any disclaimer, the term of this patent is extended or adjusted under 35 U.S.C. 154(b) by 113 days.

(21) Appl. No.: 16/810,441

(22) Filed: Mar. 5, 2020

(65) Prior Publication Data

US 2020/0246269 A1     Aug. 6, 2020

Related U.S. Application Data

(62) Division of application No. 16/353,303, filed on Mar. 14, 2019, now Pat. No. 10,617,645, which is a division of application No. 14/112,622, filed as application No. PCT/CA2012/050220 on Apr. 5, 2012, now Pat. No. 10,285,942.

(60) Provisional application No. 61/472,944, filed on Apr. 7, 2011.

(51) Int. Cl.
| | |
|---|---|
| *A61K 39/21* | (2006.01) |
| *C07K 14/16* | (2006.01) |
| *A61K 39/12* | (2006.01) |
| *C07K 14/005* | (2006.01) |
| *A61K 39/00* | (2006.01) |
| *C07K 14/74* | (2006.01) |
| *A61P 37/04* | (2006.01) |
| *A61P 31/18* | (2006.01) |
| *A61K 9/14* | (2006.01) |

(52) U.S. Cl.
CPC .............. *A61K 39/21* (2013.01); *A61K 39/12* (2013.01); *C07K 14/005* (2013.01); *C07K 14/161* (2013.01); *C07K 14/163* (2013.01); *A61K 9/14* (2013.01); *A61K 2039/53* (2013.01); *A61K 2039/54* (2013.01); *A61K 2039/55555* (2013.01); *A61K 2039/57* (2013.01); *A61P 31/18* (2018.01); *A61P 37/04* (2018.01); *C07K 14/70539* (2013.01); *C12N 2740/15034* (2013.01); *C12N 2740/16022* (2013.01); *C12N 2740/16034* (2013.01); *C12N 2740/16222* (2013.01); *C12N 2740/16234* (2013.01); *C12N 2740/16322* (2013.01); *C12N 2740/16334* (2013.01); *C12N 2760/18043* (2013.01)

(58) Field of Classification Search
CPC .. A61K 39/21; A61K 2039/53; C07K 14/005; C12N 2740/16034; C12N 2740/16234; C12N 2740/16334
See application file for complete search history.

(56) References Cited

U.S. PATENT DOCUMENTS

| 8,546,337 B2 * | 10/2013 | Burkhard | ............. C07K 14/001 514/21.3 |
|---|---|---|---|
| 2002/0182222 A1 | 12/2002 | De Groot | |

FOREIGN PATENT DOCUMENTS

| WO | WO96/20006 | 4/1996 |
|---|---|---|
| WO | WO01/24810 | 12/2001 |
| WO | WO2005/099752 | 10/2005 |
| WO | WO2009/043155 | 9/2009 |

OTHER PUBLICATIONS

Hokey, D. A. and D. B. Weiner, 2006, DNA vaccines for HIV: challenges and opportunities, Springer Semin. Immun. 28:267-279.*
Ulmer, J. B., et al., 2012, RNA-based vaccines, Vaccine 30:4414-4418.*
Li, L., et al., 2012, The future of human DNA vaccines, J. Biotechnol. 162:171-182.*
Pollard, C., et al., Dec. 2013, Challenges and advances towards the rational design of mRNA vaccines, Trends Mol. Med. 19(12):705-713.*
N. Frahm et al "Conistent Cytotoxic T Lumphocyte Targeting of Immunodominant Regions in Human Immunodeficiency Virus Across Multiple Ethnicities" Journal of Virology vol. 78, No. 5 Mar. 1, 2004 pp. 2187-2200.
M. Luo et al "For Protection from HIV-1 infection, More Might not be Better: a Systematic Analysis of HIV Gag Epitopes of Two Alleles Associated with Different Outcomes of HIV-1 Infection" Journal of Virology vol. 86 No. 2 Jan. 15, 2012, pp. 1166-1180.

(Continued)

*Primary Examiner* — Jeffrey S Parkin
(74) *Attorney, Agent, or Firm* — Michael R Williams; Ryan W Dupeds; Ade & Company, Inc.

(57) ABSTRACT

Instead of generating immune responses to several HIV proteins and risk over activating more CD4+ T cells (easy targets for HIV-1 infection) as current candidate vaccines try to do, a lower magnitude, narrowly focused, well maintained virus specific CD8+ T cell response to multiple subtypes should destroy and eliminate a few founder viruses without inducing inflammatory responses that may activate more CD4+ T cells and provide more targets for HIV-1 virus infection. Specifically, described herein is a method that focuses the immune response to the 12 protease cleavage sites.

5 Claims, 13 Drawing Sheets

Specification includes a Sequence Listing.

(56) References Cited

OTHER PUBLICATIONS

Luo Ma et al "Immunogenicity of Sequences around HIV-1 protease cleaveage sites: potential targets and popluation coverage analysis for HIV vaccine targeting protease cleaveage sites" Vaccine, vol. 31 No. 29 May 10, 2013 pp. 3000-3008.
Karlsson, Ingrid et al Identification of 1, 3, 5, 7 Conserved Subdominant HIV type 1 CDS and T cell epitopes Restricted within common HLA supertypes for therapeutic HIV type Vaccines—Aids Research and Human Retroviruses vol. 28, No. 11 pp. 1434-1443.

* cited by examiner

METHODS OF INDUCING AN IMMUNE RESPONSE AGAINST HIV-1 UTILIZING NUCLEIC ACIDS ENCODING POLYPEPTIDES CONTAINING HIV-1 PROTEASE CLEAVAGE SITES

PRIOR APPLICATION INFORMATION

The instant application is a divisional application of U.S. Ser. No. 16/353,303, filed Mar. 14, 2019, the entire contents of which are incorporated herein by reference, now U.S. Pat. No. 10,617,645, which was a divisional application of U.S. Ser. No. 14/112,622, filed Aug. 25, 2014 and entitled "Protease Cleavage Site Peptides as an HIV Vaccine", now U.S. Pat. No. 10,285,942, the contents of which are incorporated herein by reference, which was a 371 of PCT Application PCT CA2012/050220, filed Apr. 5, 2012, which claimed the benefit of U.S. Provisional Patent Application Ser. No. 61/472,944, filed Apr. 7, 2011.

FIELD OF THE INVENTION

The present invention relates to reagents and methods for preventing and treating HIV-1 infections.

BACKGROUND OF THE INVENTION

Even though it has been more than twenty-five years since the discovery of HIV, an effective preventative vaccine remains elusive. Current candidate vaccines to HIV-1 fail to provide protection and in many cases actually enhance infection. This has been attributed to the inherent difficulties of confronting a virus infecting the cell that is the key component of immune system and the challenges of a pathogen with great diversity and rapid mutation. More critically, these vaccines were developed based on conventional views of virus infection that did not reflect a sufficient understanding of the correlates of protection against HIV-1. Improving such understanding is essential to any successful vaccine development.

Heterogeneity in susceptibility to HIV-1 infection has been observed in several cohort studies. Despite repeated exposures, some individuals do not appear to become infected with HIV-1. Understanding why these individuals can escape HIV-1 infection and how their immune system works will help to reveal parameters of protective immunity and thus the development of effective vaccines and control strategies.

A subset of women in the Pumwani Sexworker cohort, established in 1985 in Nairobi, Kenya, remains HIV-1 seronegative and PCR-negative despite repeated exposure to the virus through active sexwork. Studies showed that this resistance to HIV-1 infection is associated with several alleles of Human Leukocyte Antigens (HLAs) and specific $CD8^+$ and $CD4^+$ T-cell responses to HIV-1 (Alimonti et al., 2996, Immunol Cell Biol 84: 482-485; Alimonti et al., 2005, J Infect Dis 191: 20-24; Hardie et al., 2008, Aids 22: 2038-2042; Hardie et al., 2008, Aids 22: 807-816; Lacap et al., 2008, Aids 22: 1029-1038; Rowland-Jones et al., 1995, Nat Med 1: 59-64; Rowland-Jones et al., 1998, J Clin Invest 102: 1758-1765). HLAs are a group of host proteins that are central in regulating the immune response through the binding and presenting of peptides known as epitopes derived from self and foreign proteins to T cells. The genes coding for HLAs are extremely polymorphic, resulting in a diversity of HLA alleles with variable ability and affinity for the self and pathogenic proteins in the population. This genetic diversity ensures that no pathogens can escape detection at the population level. The contribution of different HLA alleles to virus control varies because of differences in antigenic recognition. The association of HLA alleles with different outcomes of HIV-1 infection are most likely due to the differences in the antigenic peptides or epitopes of HIV being presented and the resulting immune responses that are engaged following immune recognition. Therefore, differences in the recognition of peptides/epitopes between HLA alleles associated with different outcomes of HIV-1 infection might point to a vital clue for developing an HIV-1 vaccine. The iTopia™ antigen discovery system, a novel biochemical CTL epitope discovery system, uses an MHC-peptide complex-specific antibody to assess MHC-peptide binding, relative affinity and complex stability. It permits rapid screening of large peptide libraries for multiple HLA Class I molecules (Luo et al., 2011, J Virol). In preliminary work using the iTopia epitope discovery system combined with IFN-γ CD8 ELISPOT™ assays, 616 9-mer peptides overlapping Gag of HIV-1 subtype A and D for two HLA alleles associated with different outcome of HIV-1 infection were screened. A*01:01 is significantly associated with HIV-1 resistant women (p=0.016, odds ratio: 1.7, 95% CI: 1.1-2.7) and slower rate of seroconversion (FIG. 1-A), while B*07:02 is associated with susceptibility to HIV-1 infection (p=0.035, odds ratio: 0.38, 95% CI: 0.14-1.1), rapid seroconversion (FIG. 1-B) in the Pumwani Sexworker Cohort, as well as high viral loads and rapid disease progression in several different populations. As expected, the gag epitopes of A*01:01 do not overlap with the epitopes of B*07:02. However, to our surprise, B*07:02, a allele associated with rapid seroconversion and disease progression, binds 29 peptides spanning the entire gag peptide with high to moderate affinity and low off-rate, whereas A*01:01 only binds to one peptide with relatively high affinity and normal off-rate, and with weak binding to 2 other peptides. Contrary to the conventional view of protective immunity that the tried (and failed) HIV-1 vaccines followed, which is a pan and strong immune response to several HIV-1 proteins (Nature (2007) 499: 390; AIDS Alert (2003) 18: 43-45; McCarthy 2003, Lancet 361: 755-756; Pal et al., 2002, J Virol 76: 292-302; Plotkin, Hum Vaccin 6; Vaccari et al., Expert Rev Vaccines 9: 997-1005; Wilyard, Nature 466: S8), the allele, which recognizes more epitopes and generates strong IFN-gamma ELISPOT responses, is associated with a bad outcome to HIV-1 infection.

At least two things can be learned from this observation: a) since the pan, strong immune responses do not provide protection, an anti-HIV-1 vaccine must not induce them; b) an anti-HIV vaccine must be selective and not target entire HIV-1 proteins. What should be the target? The A*01:01 gag epitope provided a clue. The only gag peptide recognized by A*01:01 with relative high affinity and normal off-rate (ED50:1.211E-5, half life:0.995 h) is a 9-mer peptide covers the protease cleavage site at p17/p24 (Luo et al., J Virol 86). This region is relatively conserved among major HIV subtypes (A1, B, D, G). We tested 8 peptide variants of these subtype consensus and found that A*01:01 can bind to all of them with similar affinity and off-rates (ED50: 4.3E-6 to1.21E-5, half life: 0.385 to1.298 h). Why is this region important for HIV-1? The protease of HIV-1 is a small 99-amino acid aspartic enzyme that mediates the cleavage of Gag, Gag-Pol and Nef precursor polyproteins. The process is highly specific, temporally regulated and essential for the production of infectious viral particles. A total of twelve proteolytic reactions are required to generate a viable virion.

SUMMARY OF THE INVENTION

According to an aspect of the invention, there is provided a purified or isolated peptide consisting of an amino acid sequence as set forth in any one of SEQ ID NO: 1-12.

According to a further aspect of the invention, there is provided a nanoparticle comprising a peptide consisting of an amino acid sequence as set forth in any one of SEQ ID NO: 1-12.

According to yet another aspect of the invention, there is provided a method of eliciting an immune reaction in an individual comprising administering to an individual in need of such treatment an effective amount of a peptide consisting of an amino acid sequence as set forth in any one of SEQ ID NO: 1-12.

According to a further aspect of the invention, there is provided a method of preparing a medicament for eliciting an immune response against human immunodeficiency virus (HIV-1) comprising admixing an isolated peptide consisting of an amino acid sequence as set forth in any one of SEQ ID NO: 1-12 and a suitable excipient for eliciting an immune response against HIV-1.

According to another aspect of the invention, there is provided a purified or isolated nucleic acid molecule encoding an amino acid sequence as set forth in any one of SEQ ID NO: 1-12.

According to a further aspect of the invention, there is provided a method of eliciting an immune reaction in an individual comprising administering to an individual in need of such treatment an effective amount of a nucleic acid molecule encoding an amino acid sequence as set forth in any one of SEQ ID NO: 1-12.

According to another aspect of the invention, there is provided a method of preparing a medicament comprising admixing a nucleic acid molecule encoding an amino acid sequence as set forth in any one of SEQ ID NO: 1-12 and a suitable excipient for eliciting an immune response against HIV-1.

BRIEF DESCRIPTION OF THE DRAWINGS

FIG. 1. HLA class I allele A*01 is independently associated with resistance to HIV-1 acquisition in the Pumwani Sexworker cohort. Women with A*01 seroconverted significantly slower than women without A*01 whereas B*07:02 is associated with rapid seroconversion. Women with B*07:02 seroconverted significantly faster than women without B*07:02. These associations are independent from other HLA class I alleles by Cox regression analysis. The enrolment year and age of women with or without these alleles are very similar.

DESCRIPTION OF THE PREFERRED EMBODIMENTS

Figure 1:
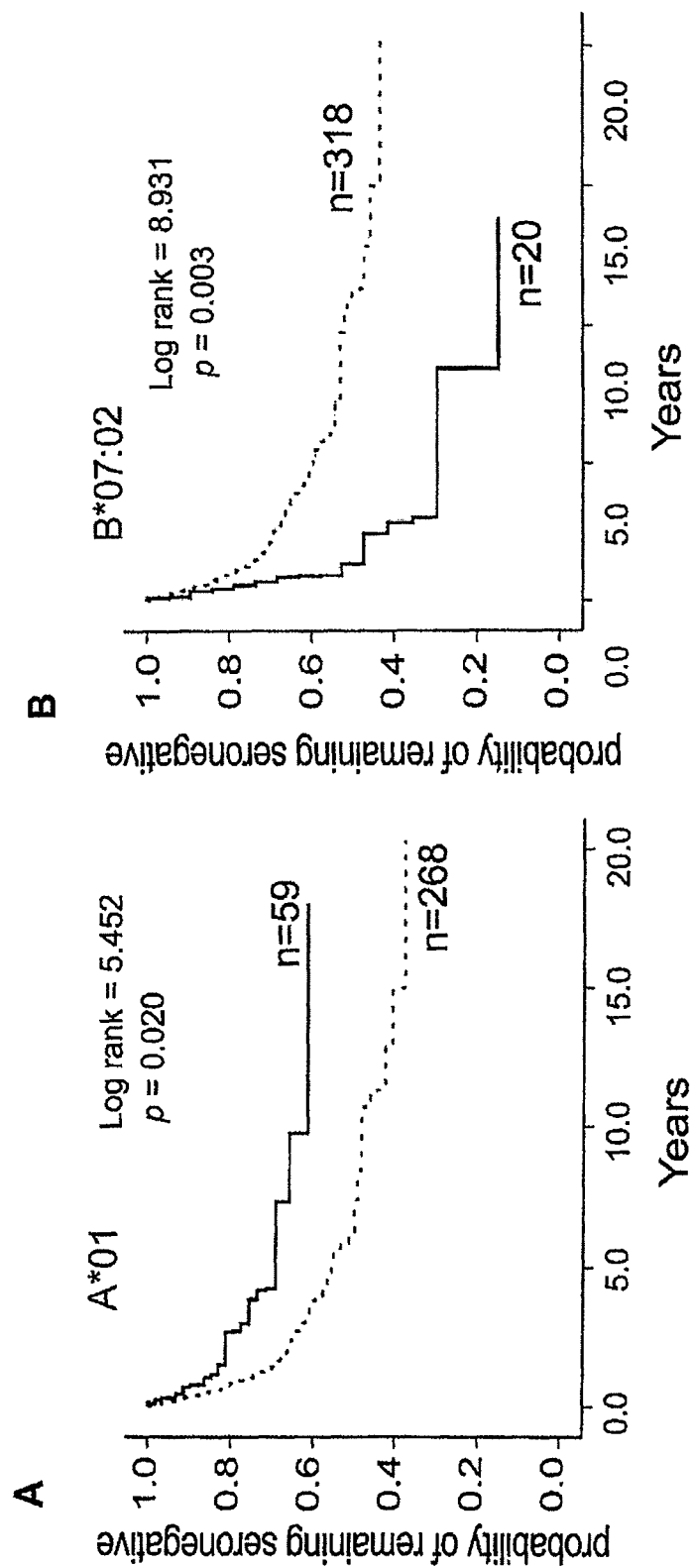

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Because of its essential role in the production of infectious virions, HIV protease has been the major therapeutic target against AIDS. Protease inhibitors have been successfully used to treat HIV-1 infection and are an essential component of successful HAART therapies (Anderson et al., 2009, Handb Exp Pharmacol 85-110). Most of the protease inhibitors were designed to compete with the protease's natural substrates based on the structure of the active binding site (Debouck 1992, AIDS Res Hum Retroviruses 8: 153-164; Laco et al., 1997, Biochemistry 36: 10696-10708; McDonald et al., 1997, Arch Intern Med 157: 951-959; Wlodawer et al., 2000, Biochim Biophys Acta 1477: 16-34; Wlodawer et al., 1998, Ann Rev Biophys Biomol Struct 27: 249-284). Recently, drugs that target Gag by preventing protease mediated processing at specific Gag cleavage sites have been developed (Adamson et al., 2009, Mol Intery 9: 70-74; Adamson et al., 2010, Antiviral Res 85: 119-141; Adamson et al., 2008, Drug Discov Today 13: 424-432; Adamson et al., 2009, Expert Opin Ther Targets 13: 895-908; Keller et al., 2010, J Virol 85: 1420-1428). Studies have shown that the process of protease cleavage requires a tightly controlled, ordered sequence of proteolytic processing events mediated by different rates of cleavage at the different processing sites (Muller et al., 2009, J Biol Chem 284: 29692-29703; Pettit et al., 2005, J Virol 79: 10601-10607; Pettit et al., 2004, J Virol 78: 8477-8485; Pettit et al., 2002, J Virol 76: 10226-10233; Pettit et al., 2005, Retrovirology 2: 66; Pettit et al., 1994, J Virol 68: 8017-8027; Wiegers et al., 1998, J Virol 72: 2846-2854). Even subtle disturbances may be sufficient to interrupt this delicately balanced process and drive it toward a non-productive end (Kaplan et al., 1993, J Virol 67: 4050-4055; Muller et al., 2009, J Biol Chem 284: 29692-29703; Pettit et al., 2005, J Virol 79: 10601-10607; Pettit et al., 2005, Retrovirology 2: 66).

Since the protease cleavage sites are highly conserved among major subtypes of HIV-1, direct immune responses against these cleavage sites would yield several advantages. First, the host immune response may destroy the virus before it can establish itself permanently in the host. Second, the vaccine could force the virus to accumulate mutations, eliminating the normal function of the HIV protease and thus eliminating viable virions. Third, limiting immune responses to these sites avoids immune responses that often generate unwanted inflammatory responses and excessive immune activation which lead to more targets for HIV-1 infection, establishment and spread.

Based on the correlates of protection from HIV in highly exposed but uninfected sex workers in the Pumwani cohort, it is hypothesized that to prevent HIV-1 acquisition, a vaccine should achieve all of the following: 1) focus on the key sites of HIV-1 instead of whole Gag and/or Env protein; 2) recognize multiple HIV subtypes; 3) avoid excess immune activation. A vaccine targeting the 12 protease cleavage sites will achieve this by restricting the immune response to the key sites of HIV-1, force the virus to mutate to its disadvantage and avoid excess immune activation. As discussed herein, the classical vaccine approach, which is aimed at generating strong immune response to full Gag and Env of HIV-1, does not take into account the potential adverse impact of generating wide spread immune responses to HIV antigens on creating enhanced susceptibility to HIV-1 virus, especially activated CD4+ T cells. In addition, since not all CD8+ T cell responses are equally effective, the effective T cell responses could be distracted by ineffective T cell responses and be neutralized by the side effects of excess immune activation, which will attract more target cells for HIV-1 as a result of the induced inflammatory responses.

As discussed herein, one novel vaccine strategy is to target the function of HIV-1 protease. Protease cleavage sites (PCS) of HIV-1 are highly conserved amongst the major subtypes and proper cleavage of all 12 protease recognition sites is needed to generate a viable virion. Directing immune responses against these cleavage sites could destroy the virus before it can establish itself in the host. Alternatively, it would force the virus to accumulate mutations at the PCSs, thus eliminating the ability of the protease to generate infectious virions. As discussed herein, we generated immune responses to peptides corresponding to 12 PCSs of SIVmac239 using a vesicular stomatitis viral (VSV) vector to test the feasibility of this vaccine approach.

Understanding that infection of CD4+ T cells, a key component of the immune system, is the key difference between HIV-1 and other infectious pathogens and activated CD4+ T cells are easier targets for HIV-1 infection is the key to designing vaccines eliciting a narrow spectrum of epitope presentation. Theoretically, recognizing more epitopes will activate more CD8+ T cells to destroy the virus infected cells. However, this could also activate more CD4+ T cells through secretion of cytokines. Because increased CD4+ T cell activation and recruitment to mucosal sites has the potential to enhance HIV transmission, this could explain why B*07:02, an allele that can recognize a broad spectrum of Gag epitopes, is associated with rapid seroconversion.

Instead of generating immune responses to several HIV proteins and risk over activating more CD4+ T cells (easy targets for HIV-1 infection) as current candidate vaccines try to do, a lower magnitude, narrowly focused, well maintained virus specific CD8+ T cell response to multiple subtypes should destroy and eliminate a few founder viruses without inducing inflammatory responses that may activate more CD4+ T cells and provide more targets for HIV-1 virus infection. Specifically, described herein is a method that focuses the immune response to the 12 protease cleavage sites. Unlike antiprotease drug approaches, this method generates host immune responses that target the 12 protease cleavage sites (p17/24, p24/p2, p2/p7, p7/p1, p1/p6, p7/TFP, TFP/p6, P6/PR, PR/RTp51, RT/RTp66, RTp66/INT, NEF). This method aims at eliminating HIV by destroying infected cells and preventing proper viral processing. As discussed herein, anti-protease drugs force mutations in the active site of the protease; cleavage site mutations to evade the antibody and T cell responses should still result in mutations which prevent efficient viral protein processing.

To test the feasibility of this vaccine approach, we used 12 VSV-peptide viruses (IM immunization) and nanopackaged peptides (intranasal boost) as immunogens and 18 Cynomolgus macaques/SIVmac239. As discussed herein, this showed that VSV-peptides immunization and nano-packaged peptide boost generated both antibody and T cell responses to the 12 peptides overlapping the 12 protease cleavage sites and immune responses to the specific peptides depends on the MHC of the monkeys. We used a cumulative, accelerated high dose SIVmac239 intrarectal challenge (1000, 2000, and 3×4000 $TCID_{50}$) to examine whether immune response to the 12 protease cleavage sites can protect macaques from SIV infection. Results showed that after a cumulative 7000 TCID$_{50}$ challenge, monkeys with immune responses to one or more of the 12 peptides are better protected from SIVmac239 infection when compared to the controls which received no immunization and the monkeys without immune responses to the peptides (Odds ratio: 13.3, 95% CI: 1.05-169.6, p=0.047, Fisher's exact). Preliminary analysis of plasma antibodies to the peptides of the 12 protease cleavage sites showed that macaques with antibody responses to more peptides are better protected from the higher dose of SIVmac239 challenge (p=0.012). Thus, generating immune responses specifically targeting the 12 protease cleavage sites can protect the macaques from high dose SIVmac239 mucosal challenge.

Non-human primates (NHPs) are important and arguably the best animal models to evaluate the safety and efficacy of candidate vaccines against human pathogens and study the pathogenesis of infectious and immune-mediated diseases, because they are immunologically similar to humans and are susceptible to many of the same pathogens (Bontrop, R. E., Non-human primates: essential partners in biomedical research. Immunol Rev, 2001. 183: p. 5-9.). Among the nonhuman primates Cynomolgus macaques (*Macaca fascicularis*) are a common model for pathogenesis studies and are more readily available than Rhesus macaques. They are widely used in many infectious disease studies, including TB, Ebola, Dengue, SIV and HIV (Walsh, G. P., et al., Nat Med, 1996. 2(4): p. 430-6; Larsen, M. H., et al., Vaccine, 2009. 27(34): p. 4709-17; Okada, M., et al., Vaccine, 2009. 27(25-26): p. 3267-70; Pawar, S. N., et al., AIDS Res Hum Retroviruses, 2008. 24(4): p. 643-54; Kita, Y., et al., Vaccine, 2005. 23(17-18): p. 2132-5; Qiu, X., et al., PLoS One, 2009. 4(5): p. e5547; Geisbert, T. W., et al., J Virol, 2009. 83(14): p. 7296-304; Geisbert, T. W., et al., Vaccine, 2008. 26(52): p. 6894-900; Warfield, K. L., et al., J Infect Dis, 2007. 196 Suppl 2: p. S430-7; Swenson, D. L., et al., Clin Vaccine Immunol, 2008. 15(3): p. 460-7; Sullivan, N.J., et al., PLoS Med, 2006. 3(6): p. e177; Feldmann, H., et al., Nat Rev Immunol, 2003. 3(8): p. 677-85; Clarke, T. and J. Knight, Nature, 2003. 424(6949): p. 602; Ikegami, T., Exp Anim, 2002. 51(5): p. 447-55; Garbutt, M., et al., J Virol, 2004. 78(10): p. 5458-65; Angsubhakorn, S., et al., Trans R Soc Trop Med Hyg, 1988. 82(5): p. 746-9; Bernardo, L., et al., Clin Vaccine Immunol, 2008. 15(3): p. 439-46; Guy, B., et al., Am J Trop Med Hyg, 2009. 80(2): p. 302-11; Bernardo, L., et al., Antiviral Res, 2008. 80(2): p. 194-9; Koraka, P., et al., Vaccine, 2007. 25(29): p. 5409-16; Koraka, P., et al., Microbes Infect, 2007. 9(8): p. 940-6; Butrapet, S., et al., Southeast Asian J Trop Med Public Health, 2002. 33(3): p. 589-99; Nakayama, E. E. and T. Shioda, Rev Med Virol. 20(2): p. 77-92; Jiang, Y., et al., J Med Primatol, 2009. 38 Suppl 1: p. 39-46; Turbant, S., et al., Vaccine, 2009. 27(39): p. 5349-56; Bourry, O., et al., Aids, 2009. 23(4): p. 447-54; Kamada, K., et al., Microbes Infect, 2009. 11(2): p. 164-71; Morner, A., et al., J Virol, 2009. 83(2): p. 540-51; Malleret, B., et al., Blood, 2008. 112(12): p. 4598-608; Dahl, M. E., et al., J Pharmacol Exp Ther, 2008. 327(3): p. 926-33; Brennan, G., Y. Kozyrev, and S. L. Hu, Proc Natl Acad Sci USA, 2008. 105(9): p. 3569-74; Vieillard, V., et al., Proc Natl Acad Sci USA, 2008. 105(6): p. 2100-4; Vieillard, V., et al., Aids, 2008. 22(2): p. 185-92; Prost, S., et al., J Clin Invest, 2008. 118(5): p. 1765-75; Karlsson, I., et al., J Virol, 2007. 81(24): p. 13456-68.) As discussed herein, peptides that correspond to the cleavage site of the HIV-1 protease and may be used in a vaccine preparation include:

| | |
|---|---|
| | (SEQ ID NO: 1) |
| p17(MA)/p24(CA): | GNSSKVSQNYPIVQNLQGQM; |
| | (SEQ ID NO: 2) |
| p24(CA)/P2: | GGPSHKARVLAEAMSQVTNT; |
| | (SEQ ID NO: 3) |
| p2/p7(NC): | MSQVQHTNIMMQRGNFKGQKI; |
| | (SEQ ID NO: 4) |
| p7(NC)/p1: | MKDCTERQANFLGKIWPSNK; |
| | (SEQ ID NO: 5) |
| p1/p6gag: | PSHKGRPGNFLQSRPEPTAP; |
| | (SEQ ID NO: 6) |
| p7(NC)/TFP: | MKDCTERQANFLRENLAFQQ; |
| | (SEQ ID NO: 7) |
| TFP/p6pol: | ANFLRENLAFQQGEAREFSS; |
| | (SEQ ID NO: 8) |
| P6pol/PR | ERQGTVSFSFPQITLWQRPL; |
| | (SEQ ID NO: 9) |
| PR/RTp51 | LTQIGCTLNFPISPIETVPV; |
| | (SEQ ID NO: 10) |
| RT/RTp66 | KEPIA(I)GAETFYVDGAANRET; |
| | (SEQ ID NO: 11) |
| RTp66/INT and | LVSNGIRKVLFLDGIDKAQE; |
| | (SEQ ID NO: 12) |
| Nef | TAQTNPDCAWLEAQEEEEVG. |

According to an aspect of the invention, there is provided a purified or isolated peptide consisting of an amino acid sequence as set forth in any one of SEQ ID NO: 1-12. In a preferred embodiment, the purified or isolated peptide consists of the amino acid sequence as set forth in SEQ ID NO: 1.

According to another aspect of the invention, there is provided a nanoparticle comprising a peptide consisting of the amino acid sequence as set forth in any one of SEQ ID NO: 1-12. In a preferred embodiment, the nanoparticle comprises 12 distinct peptides, a respective one having an amino acid sequence as set forth in a respective one of SEQ ID NO: 1-12.

As used herein, "purified" does not necessarily mean absolute purity but rather means that the peptide has been purified or enriched by 2, 4, 10, 20, 100 fold or more.

As used herein, "isolated" means that the peptide has been removed from its natural environment.

For synthetic peptides, "purified" or "isolated" may mean for example that the components associated with peptide synthesis have been substantially removed.

According to another aspect of the invention, there is provided the use of a peptide consisting of the amino acid sequence as set forth in any one of SEQ ID NO: 1-12 for eliciting an immune response in an individual in need of such treatment.

As used herein, "an individual in need of such treatment" refers to an individual who desires protective immunity against HIV-1 infection. Such an individual may be for example an individual who has been infected with HIV-1, an individual who has recently been infected with HIV-1, an individual who is suspected of having been infected with HIV-1, a person who is at risk of infection with HIV-1 and/or an individual who desires protective immunity against HIV-1. Preferably, the individual is a human.

According to another aspect of the invention, there is provided a method of eliciting an immune reaction in an individual comprising administering to an individual in need of such treatment an effective amount of a peptide consisting of the amino acid sequence as set forth in any one of SEQ ID NO: 1-12.

According to another aspect of the invention, there is provided a method of preparing a medicament comprising admixing an isolated peptide consisting of the amino acid sequence as set forth in any one of SEQ ID NO: 1-12 and a suitable excipient for eliciting an immune response against HIV-1.

According to another aspect of the invention, there is provided a medicament for eliciting an immune response against HIV-1 in an individual comprising a peptide consisting of the amino acid sequence as set forth in any one of SEQ ID NO: 1-12 and a suitable excipient.

According to another aspect of the invention, there is provided a medicament for eliciting an immune response against HIV-1 in an individual comprising an effective amount of each of 12 peptides, each representative peptide consisting of the amino acid sequence as set forth in a respective one of SEQ ID NO: 1-12; and a suitable excipient.

In another embodiment of the invention, nucleic acid sequences encoding the above-described peptides are prepared.

As will be appreciated by one of skill in the art, because of the degeneracy of the genetic code, a number of different nucleic acid molecules can be generated which all encode a single peptide. Consequently a number of different nucleic acid molecules encoding the amino acid sequences as set forth in any one of SEQ ID NO: 1-12 can be constructed.

According to an aspect of the invention, there is provided a purified or isolated nucleic acid molecule encoding the amino acid sequence as set forth in any one of SEQ ID NO: 1-12.

As will be appreciated by one of skill in the art, in these embodiments, the nucleic acid molecule may be inserted into a vector, for example, an expression system. It is of note that many suitable expression vectors and systems will be readily apparent to one of skill in the art.

According to another aspect of the invention, there is provided the use of a purified or isolated nucleic acid molecule encoding the amino acid sequence as set forth in any one of SEQ ID NO: 1-12 for eliciting an immune response in an individual in need of such treatment.

In embodiments such as these, in which a nucleic acid molecule is used, for example, to elicit an immune response or treat an individual, it is to be understood that the nucleic acid molecule encoding the peptide is arranged for expression within the host cell. In some embodiments, the nucleic acid molecule may be "naked DNA" or the nucleic acid molecule may be inserted into a suitable vector system as discussed above and may be operably linked to a suitable promoter such that the encoded peptide is expressed in the desired cells. As discussed above and herein, such expression systems are well known in the art.

According to another aspect of the invention, there is provided a method of eliciting an immune reaction in an individual comprising administering to an individual in need of such treatment an effective amount of a nucleic acid molecule encoding the amino acid sequence as set forth in any one of SEQ ID NO: 1-12.

According to another aspect of the invention, there is provided a method of preparing a medicament comprising admixing a nucleic acid molecule encoding the amino acid sequence as set forth in any one of SEQ ID NO: 1-12 and a suitable excipient for eliciting an immune response against HIV-1.

According to another aspect of the invention, there is provided is provided a medicament for eliciting an immune response against HIV-1 in an individual comprising a nucleic acid molecule encoding the amino acid sequence as set forth in any one of SEQ ID NO: 1-12 and a suitable excipient.

According to another aspect of the invention, there is provided is provided a medicament for eliciting an immune response against HIV-1 in an individual comprising 12 nucleic acid molecules, each representative one of said nucleic acid molecules encoding the amino acid sequence as set forth in a respective one of SEQ ID NO: 1-12; and a suitable excipient.

As will be apparent to one of skill in the art, the frequency of usage of specific codons is known in many organisms. Accordingly, it is possible to develop or engineer or construct a nucleic acid molecule encoding a specific peptide using the most frequently used codons so that maximum expression of the peptide encoded by the nucleic acid molecule is achieved.

Accordingly, SEQ ID NOS: 13-24 represent codon-optimized sequences for expression in mammalian cells of the peptides encoded by the amino acid sequences set forth in SEQ ID NO: 1-12.

p17(MA)/p24(CA):
(SEQ ID NO: 13)
GGCAACAGCAGCAAGGTGAGCCAGAACTACCCCATCGTGCAGAACCTGCA

GGGCCAGATG;

p24(CA)/P2:
(SEQ ID NO: 14)
GGCGGCCCCAGCCACAAGGCCAGGGTGCTGGCCGAGGCCATGAGCCAGGT

GACCAACACC;

p2/p7(NC):
(SEQ ID NO: 15)
ATGAGCCAGGTGCAGCACACCAACATCATGATGCAGAGGGGCAACTTCAA

GGGCCAGAAG;

p7(NC)/p1:
(SEQ ID NO: 16)
ATGAAGGACTGCACCGAGAGGCAGGCCAACTTCCTGGGCAAGATCTGGCC

CAGCAACAAG;

p1/p6gag:
(SEQ ID NO: 17)
CCCAGCCACAAGGGCAGGCCCGGCAACTTCCTGCAGAGCAGGCCCGAGCC

CACCGCCCCC;

p7(NC)/TFP:
(SEQ ID NO: 18)
ATGAAGGACTGCACCGAGAGGCAGGCCAACTTCCTGAGGGAGAACCTGGC

CTTCCAGCAG;

TFP/p6pol:
(SEQ ID NO: 19)
GCCAACTTCCTGAGGGAGAACCTGGCCTTCCAGCAGGGCGAGGCCAGGGA

GTTCAGCAGC;

-continued

P6pol/PR:
(SEQ ID NO: 20)
GAGAGGCAGGGCACCGTGAGCTTCAGCTTCCCCCAGATCACCCTGTGGCA

GAGGCCCCTG;

PR/RTp51:
(SEQ ID NO: 21)
CTGACCCAGATCGGCTGCACCCTGAACTTCCCCATCAGCCCCATCGAGAC

CGTGCCCGTG;

RT/RTp66:
(SEQ ID NO: 22)
AAGGAGCCCATCRYCGGCGCCGAGACCTTCTACGTGGACGGCGCCGCCAA

CAGGGAGACC;

RTp66/INT:
(SEQ ID NO: 23)
CTGGTGAGCAACGGCATCAGGAAGGTGCTGTTCCTGGACGGCATCGACAA

GGCCCAGGAG;
and

Net:
(SEQ ID NO: 24)
ACCGCCCAGACCAACCCCGACTGCGCCTGGCTGGAGGCCCAGGAGGAGGA

GGAGGTGGGC.

According to an aspect of the invention, there is provided a purified or isolated nucleic acid molecule consisting of the nucleotide sequence as set forth in any one of SEQ ID NO: 13-24.

According to another aspect of the invention, there is provided the use of a nucleic acid molecule consisting of the nucleotide sequence as set forth in any one of SEQ ID NO: 13-24 for eliciting an immune response in an individual in need of such treatment.

According to another aspect of the invention, there is provided a method of eliciting an immune reaction in an individual comprising administering to an individual in need of such treatment a nucleic acid molecule consisting of the nucleotide sequence as set forth in any one of SEQ ID NO: 13-24.

An "effective amount" of the nucleic acid molecule may be an amount sufficient to generate a sufficient amount of the encoded peptide to elicit an immune response or immune reaction, for example, to elicit protective immunity.

According to another aspect of the invention, there is provided a method of preparing a medicament comprising admixing an effective amount of a nucleic acid molecule encoding the nucleotide sequence as set forth in any one of SEQ ID NO: 13-24 and a suitable excipient for eliciting an immune response against HIV-1.

According to another aspect of the invention, there is provided a medicament for eliciting an immune response against HIV-1 in an individual comprising a nucleic acid molecule consisting of the nucleotide sequence as set forth in any one of SEQ ID NO: 13-24 and a suitable excipient.

According to another aspect of the invention, there is provided is provided a medicament for eliciting an immune response against HIV-1 in an individual comprising an effective amount of 12 nucleic acid molecules, each respective one of said 12 nucleic acid molecules consisting of the nucleotide sequence as set forth in a respective one of SEQ ID NO: 13-24; and a suitable excipient.

Generating immune responses to any antigen, for example, a peptide having an amino acid sequence as set forth in any one of SEQ ID NO: 1-12 requires an efficient antigen delivery system. One advantage of using viral vectors as vaccines is that they are believed to act as their own adjuvant by stimulating the innate immune response through the binding of viral components to pathogen recognition receptors of the host cells (Clarke et al., 2006, Springer Semin Immunopathol 28: 239-253). Delivery of antigens in nanoparticles can protect antigens against degradation by enzymes, facilitate uptake by APCs, prolong presentation of antigens, induce cell-mediated immune responses, elicit more effective immune responses than soluble antigens (Csaba et al., Adv Drug Deliv Rev 61: 140-157; De Temmerman et al., 2011, Drug Discov Today 16: 569-582; Koping-Hoggard et al., 2005, Expert Rev Vaccines 4: 185-196). To test the hypotheses that an effective preventative HIV vaccine selectively targets the key sites of HIV-1 and a vaccine targeting the 12 protease cleavage sites of HIV-1 can prevent HIV-1 acquisition, we selected two antigen delivery methods: recombinant vesicular stomatitis virus and nanoparticle antigen delivery system, discussed herein.

The pATX VSVΔG4 plasmid encodes the full-length VSV virus with the exception of the native glycoprotein (GP). This virus vector was modified to tolerate the addition of four foreign genes due to the presence of four unique multiple cloning sites (MCS #1 to 4). The nucleotide sequences (SEQ ID NO: 37-48) encoding the peptide overlapping the 12 protease cleavage sites (SEQ ID NO: 25-36) were codon-optimized for expression in mammalian cells as discussed above and synthesized by PCR from complementary 40-mer oligonucleotide primers along with flanking MluI/BlnI restriction sites required for cloning into the desired location of pATX VSVΔG4. The nucleotide sequence of each peptide was cloned into PCR® 2.1-TOPO TA vector and then inserted into MCS #3 of pATX VSVΔG4 in order to facilitate stronger immune responses.

As discussed below, experiments in mice demonstrated that the peptides overlapping the 12 protease cleavage sites were successfully expressed in the recombinant viruses and that they are immunogenic. It is important to note that in these experiments, recombinant VSV particles expressing the respective peptides were used, demonstrating that expression vectors can be used for immunization.

In a study using Cynomolgus macaques from Philippines, described below, the results showed that recombinant VSV expressing peptides overlapping the protease cleavage sites can generate antibody and T cell responses in macaques, and nanopackaged peptides can boost plasma antibody and T cell response to the peptides overlapping the protease cleavage sites. The macaques with antibody and T cell response to the peptides overlapping the protease cleavage sites are better protected from higher dosage of intrarectal SIVmac239 challenges. As discussed below, macaques with antibody responses against any of the 12 peptides are better protected against higher dose intrarectal SIVmac239 challenge. A Macaque with antibody responses to 8 peptides has not been infected after a cumulative of 15000 $TCID_{50}$ SIVmac239 intrarectal challenge (1000, 2000, 4000, 4000 and 4000 $TCID_{50}$).

Furthermore, as discussed below, there is a positive correlation between antibody responses (to the number of peptides) and the infection dosage of SIVmac239 intrarectal challenge.

As discussed herein, better protection from intrarectal challenge is obtained if a low dose, such as 175 or 250 $TCID_{50}$ is used. The HIV viral load in one ejaculation in sexual transmissions is estimated at $10^4$ to $10^{-5}$ copies/ml and is equivalent to 5 to 50 $TCID_{50}$.

The immunogenicity of the peptides was also demonstrated by positive results of a peptide screen using iTopia Epitope Discovery System™ and ELISPOT™ responses in human PBMCs as discussed below.

In summary, the vaccines targeting the protease cleavage sites showed that the immune responses generated can protect macaques from an accelerated high dosage of intrarectal SIVmac239 challenge when compared with unvaccinated controls and macaques with poor immune response to the PCS-peptides. The results demonstrate that an HIV vaccine targeting the 12 protease cleavage sites (SEQ ID NO: 1-12) will be effective. Furthermore, a nano-packaged peptide cocktail that effectively generates immune responses to the PCS-peptides will reduce the time to bring the vaccine to its application: prevention from HIV-1 acquisition and stop the HIV pandemic that has caused more than 25 million deaths, more than 60 million infections and devastated social communities and the economies of countries in the pandemic region.

As discussed herein, the novel vaccine approach is derived from studying the correlate of protection of a group of highly exposed and persistently seronegative female sex workers enrolled in the Pumwani sex worker cohort. We have tested the feasibility of this approach in a pilot study by immunizing Cynomolgus macaques with 12 recombinant VSV-peptide viruses and boosted the immune responses with nano-package peptides. The monkeys were then intrarectally challenged with cumulative, accelerated high dose SIVmac239. The results showed that monkeys with immune responses to one or more protease cleavage sites are 13 times less likely to be infected by SIVmac239 mucosal challenge than the monkeys that did not receive the immunization and the monkeys that have no "good" immune responses to any of the protease cleavage sites.

The invention will now be explained and illustrated by way of examples. However, the invention is not necessarily limited by the examples.

Figure 2:
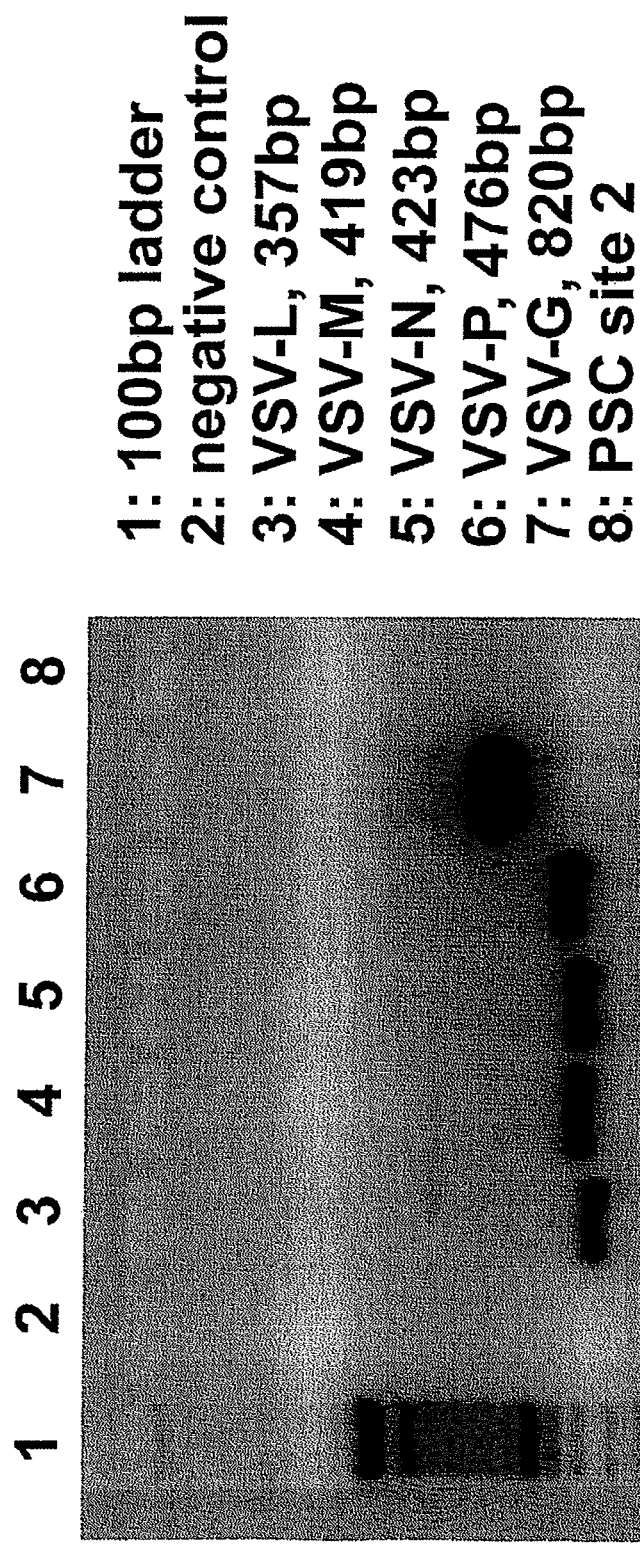
FIG. 2. Agarose gel electrophoresis of RT-PCR products. The results demonstrate the expression of RNA of peptides overlapping the p27/p2 site of protease cleavage site of SIVmac239.
Figure 3:
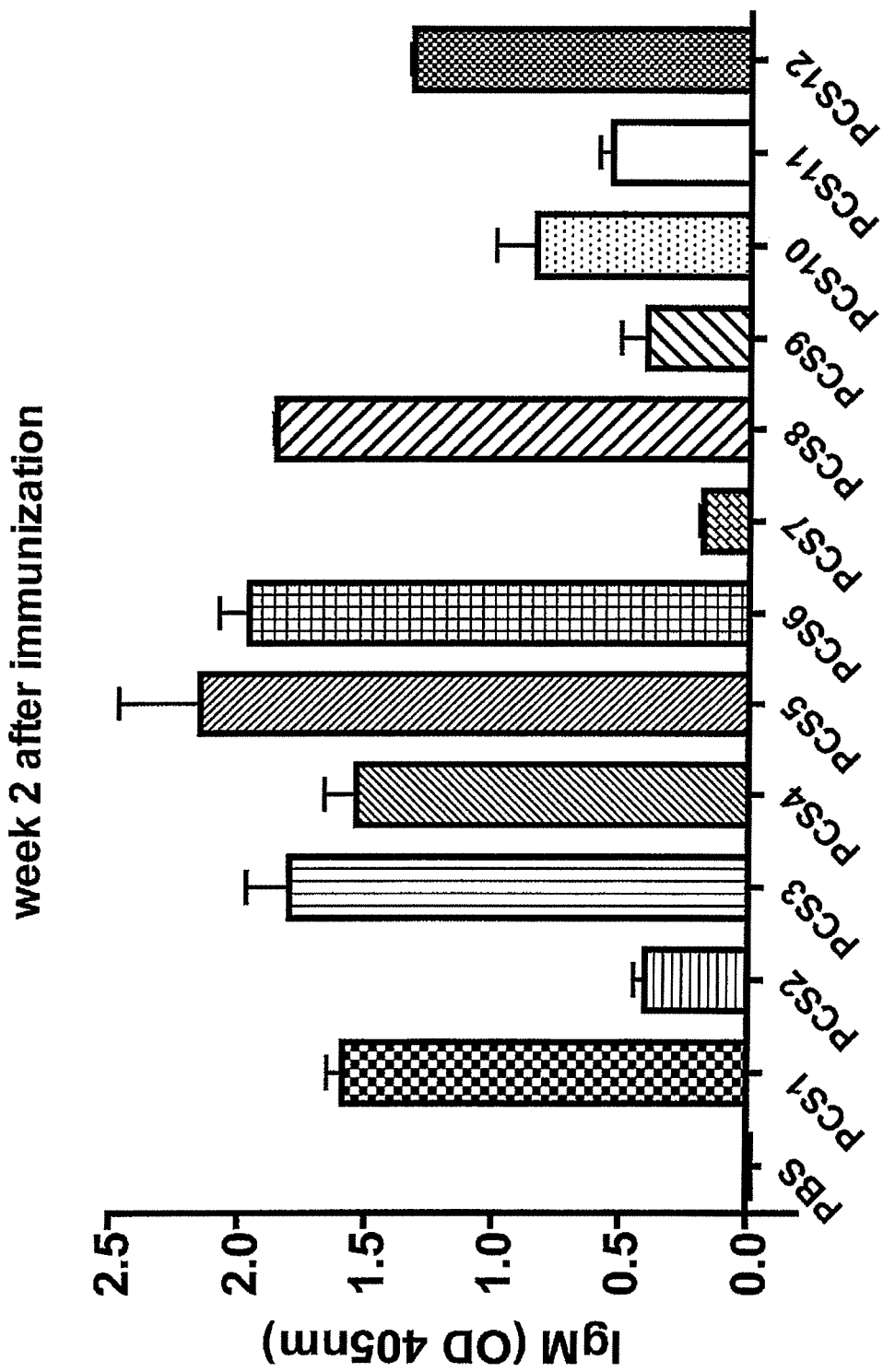
FIG. 3. IgM antibodies to the peptides overlapping the 12 protease cleavage sites were detected in BALB/c mice 2 weeks after immunization with recombinant vesicular stomatitis virus.

The nucleotide sequences (SEQ ID NO: 37-48) encoding the peptides (SEQ ID NO: 25-36) overlapping the 12 protease cleavage sites were cloned into the rVSV vector. This generated 12 recombinant VSV viruses each expressing one of the 12 20-amino acid peptides of SEQ ID NO: 1-12 respectively. RT-PCR demonstrated the expression of RNA encoding the peptides overlapping the protease cleavage sites. An example is shown in FIG. 2. Because these are short peptides (20 amino acids), it was difficult to confirm their expression by regular Western blot analysis. Consequently, an indirect method was used to confirm expression of the peptides of SEQ ID NO: 1-12 by immunizing BALB/c mice with each of the recombinant VSV-peptide virus particles and examine antibody response to the peptides. The results showed that these recombinant VSV viruses generated IgM antibody responses to the peptides in mice 2 weeks after IM immunization (FIG. 3). The results demonstrated that the peptides overlapping the 12 protease cleavage sites were successfully expressed by the recombinant viruses and that the peptides expressed by the recombinant vectors are immunogenic.

Next, nanoparticles were specifically engineered for the encapsulation of the 12 distinct peptides overlapping the protease cleavage sites (SEQ ID NO: 25-36).

Advances in nanotechnology have led to the development of nanoparticulate carriers composed of biomaterials that are biocompatible and biodegradable and can be used to efficiently deliver proteins and genes (Csaba et al., 2005 in Polymeric Gene Delivery: Principles and Applications (2005: CRC Press); de la Fuente et al., 2008, Nanomed 3: 845-857; de la Fuente et al., 2008, Marcomol Biosci 8: 441-450; Saez-Cirion et al., 2009, J Immunol 182: 7828-7837). These nanoparticles can also accommodate antigenic material and are promising agents as adjuvants for subunit vaccination (Csaba et al., 2009, Adv Drug Deliv Rev 61: 140-157; Koping-Hoggard et al., 2005, Expert Rev Vaccines 4: 185-196). Their ability to protect the antigen from environmental conditions (Petit et al., 1994, J Virol 68: 8017-8027), to pass the mucosal barrier (Petit et al., 199, J Virol 8017-8027; Saez-Cirion et al., 2009, J Immunol 182: 7828-7837; Willer et al., 2010, Nature 446:S8), and to potentiate immune responses have prompted the investigation of nanostructures for single dose and needle-free vaccination.

Nanoparticle-based vaccines have shown to be effective in the induction of immune responses. Typically, the intramuscular or intranasal administration to mice of antigens encapsulated into nanocarriers induced immune responses that significantly exceeded those provoked by the antigens alone. More recently, a pilot study involving non-human primates and SIVmac239 showed the potential of polysaccharidic nanoparticle packaged antigens to prevent HIV-1 acquisition.

Figure 4:
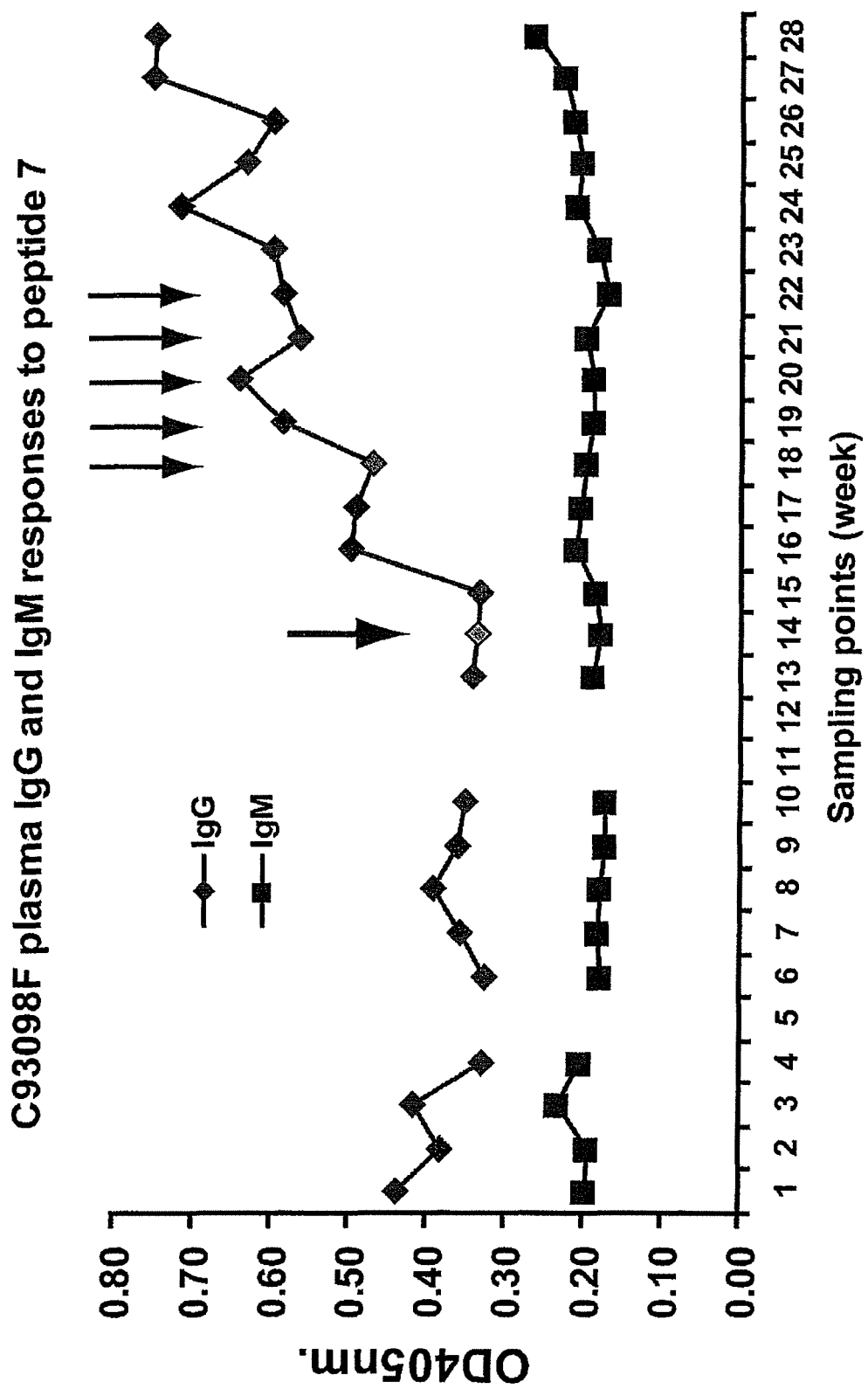
FIG. 4. Nanopackaged peptides boosted plasma antibody response to the peptide in Cynomolgus macaque C93098F. One arrow shoes the time of nasal boost with nanopackaged peptides. The second arrow shows intrarectal challenges with SIVmac239 (1000, 2000, 4000, 4000 and 4000 $TCID_{50}$). The macaque remains uninfected.
Figure 5:
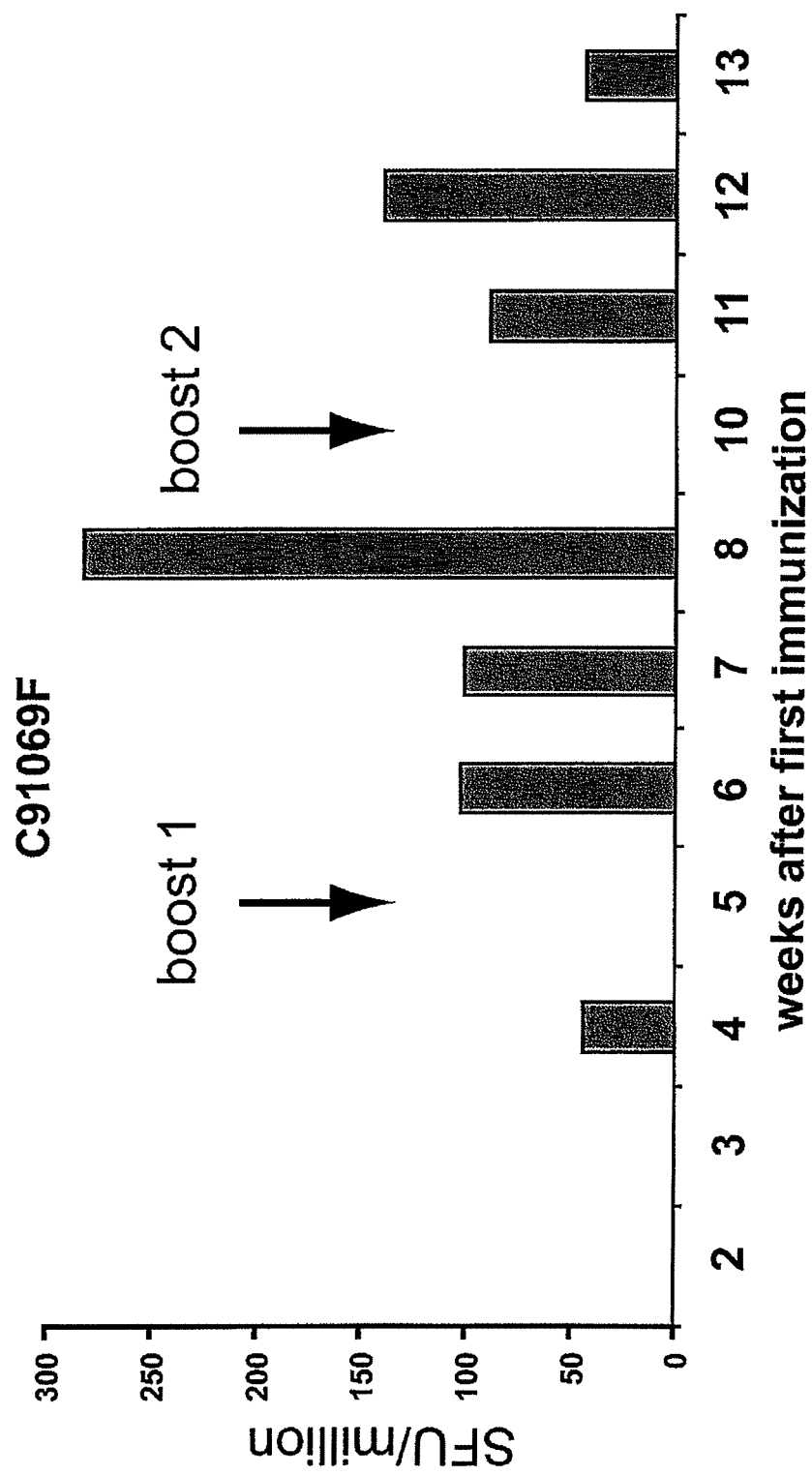
FIG. 5. Boost with nanopackaged peptides increased IFN-gamma ELISpot response to the peptides overlapping the 12 protease cleavage sites.
Figure 6:
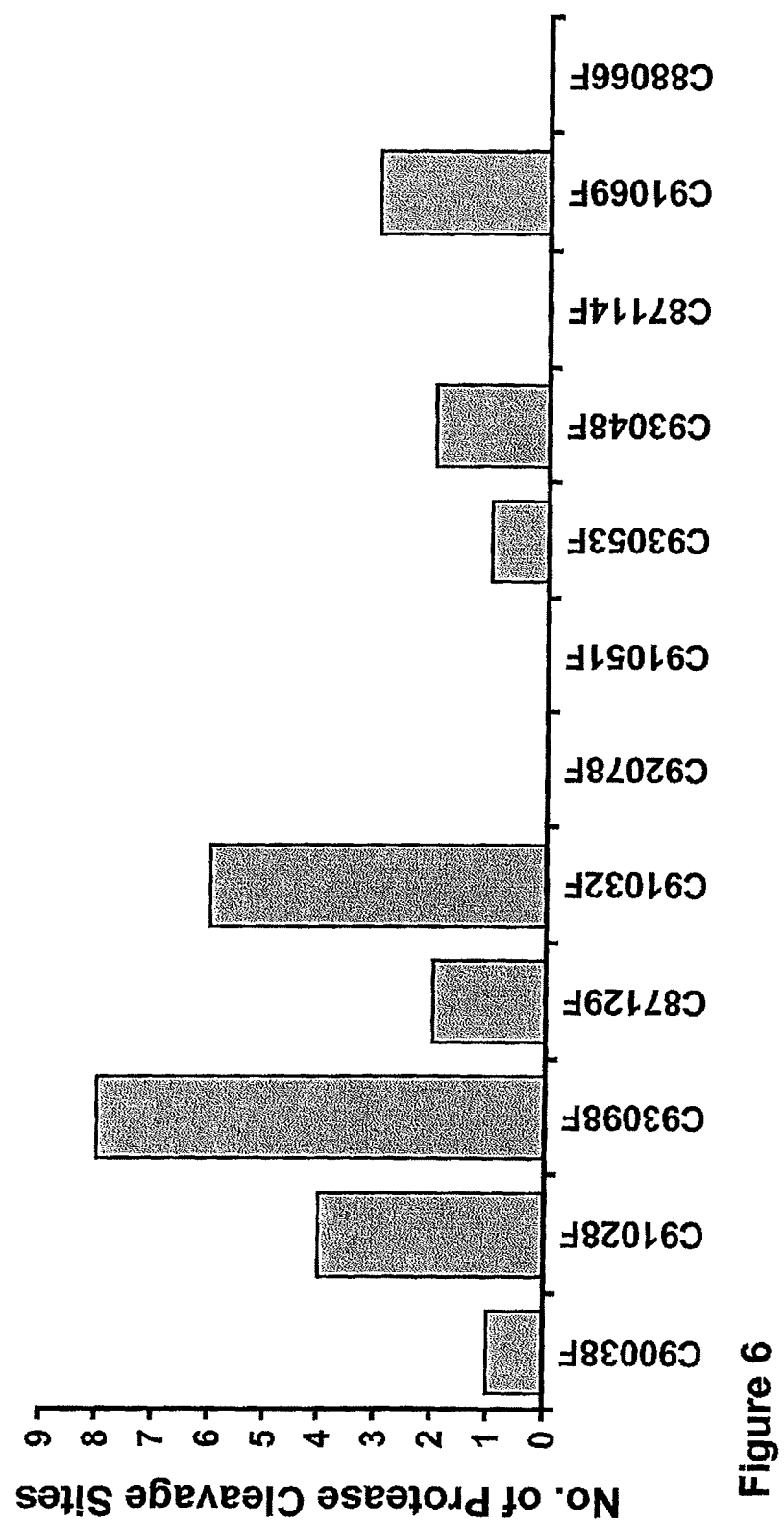
FIG. 6. Cynomolgus macaque of Philippine origin showed variable ability in recognizing peptides overlapping the 12 protease cleavage sites. The plasma antibody assays showed that the antibody response to the peptides ranges from 0 to 8 different protease cleavage sites.

Nanoparticles were specifically engineered for the encapsulation of the 12 distinct peptides overlapping the protease cleavage sites (SEQ ID NO: 25-36). The nanopackaged peptides boosted antibody and T cell responses to the peptides overlapping the protease cleavage sites (FIGS. 4 and 5). Macaques immunized with recombinant VSVs and boosted with the nanopackaged peptides showed much greater resistance to infection than unvaccinated animals.

The nanostructures are composed of biomaterials such as for example but by no means limited to polysaccharides, polyaminoacids and lipids, of pharmaceutical grade. Other suitable biomaterials and methods of production of nanostructures and nanoparticles will be readily apparent to one of skill in the art.

For example, techniques such as ionic gelification, nanoprecipitation and solvent displacement can be used to efficiently entrap the antigens within biodegradable nanocarrier particles. Based on the selected biomaterials, the antigen characteristics and the immunization objectives, nanocarriers can be developed as nanomatrices or nanocapsules containing an oily core. Of course, nanoparticles constructed with different polysaccharides, polyaminoacids and lipids will be of differing size and zeta potential. Furthermore, the loading capacity of the nanoparticles, protection and release of the associated antigens can be determined by HPLC, SDS-PAGE or Western Blot.

The effect of protection from infection was measured in the number of exposures and cumulative dose of SIVmac239 viral challenge. Secondary outcome such as viral load set point and CD4+ T cell decline was also compared. Correlation of systemic and mucosal antibody and T cell response to the antigens with protection from low-dose intrarectal SIVmac239 challenge was conducted by regression analysis. The secondary outcome including peak and set point viral load, acute and chronic CD4+ T cell counts, CD4/CD8 ratios and viral mutations were analyzed.

Figure 9:
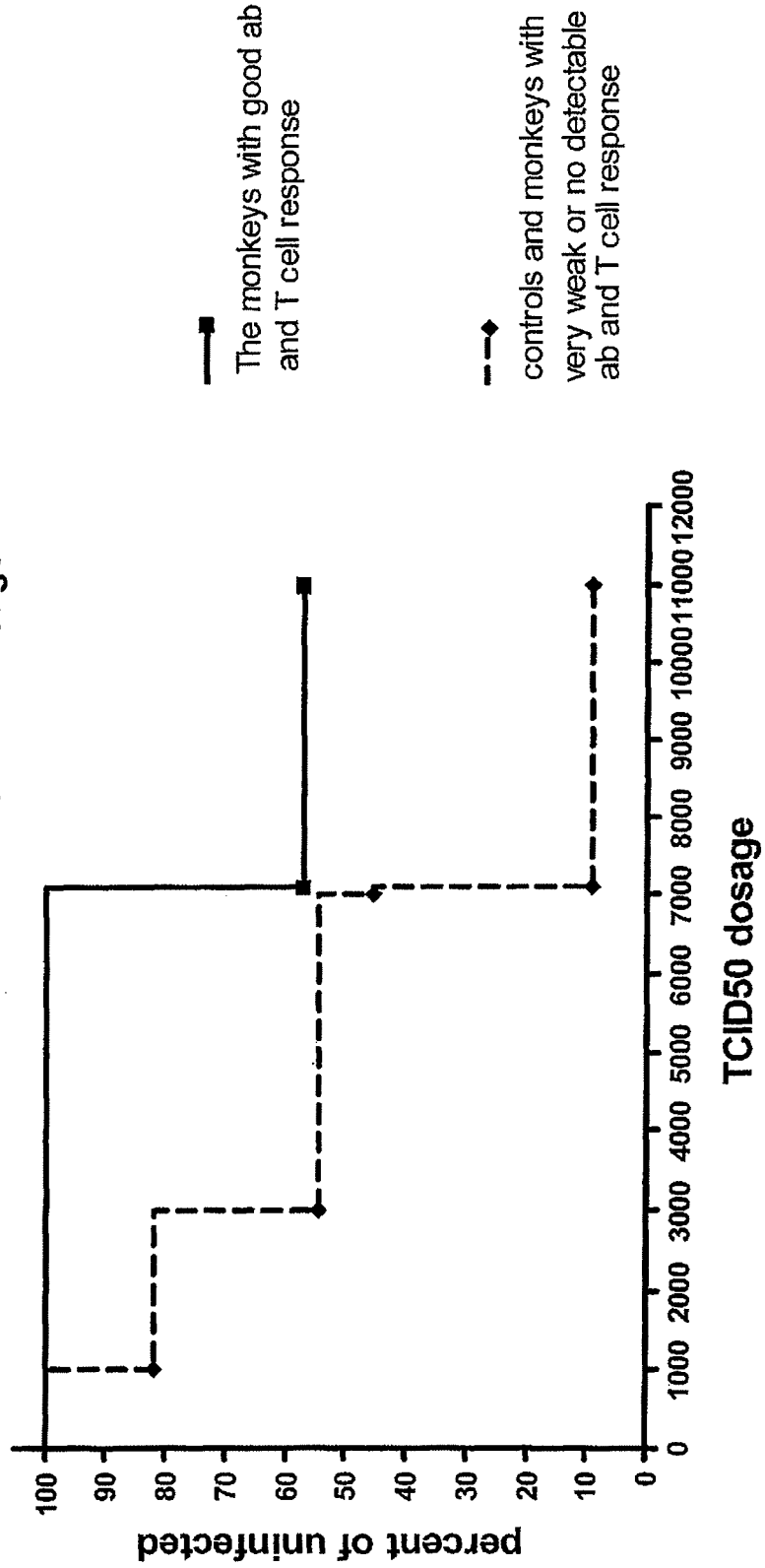
FIG. 9. Survival analysis of SIVmac239 intrarectal challenge and the odds ratio of protection for macaques with good T cell and antibody responses to the peptides overlapping the protease cleavage sites.
Figure 10:
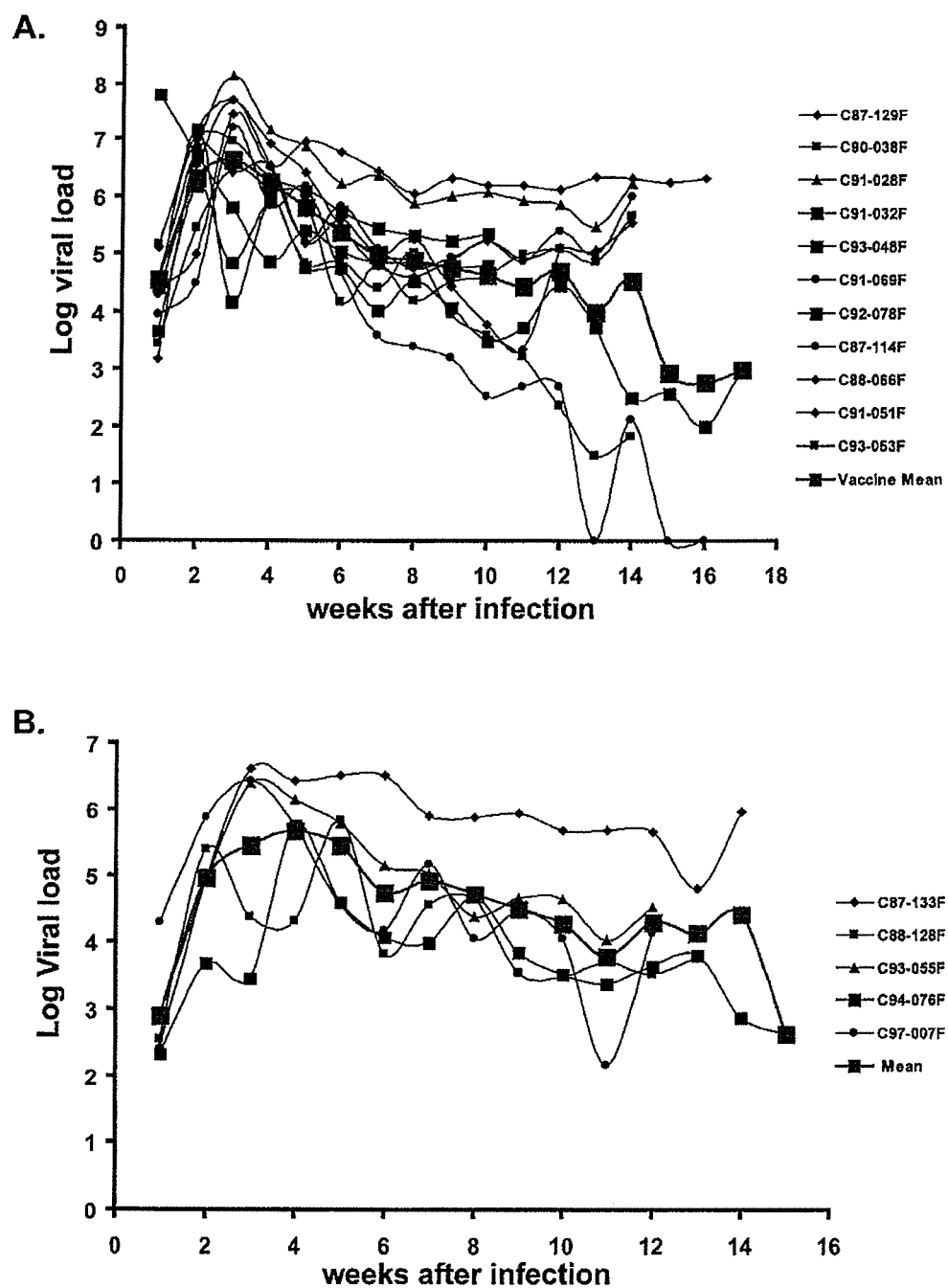
FIG. 10. Comparison of the viral load between the vaccinated group and the control group. Since the vaccinated macaques have been challenged with higher dosage of SIVmac239, it is not a fare comparison of the peak viral load. It appears that despite the higher peak viral load in the vaccinated macaques due to the higher dosage of challenge, their viral load declines much faster than the control group. A. Viral load of the Vaccinated group, B. Viral load of the Control group. Red line represents the mean viral load of the group.
Figure 11:
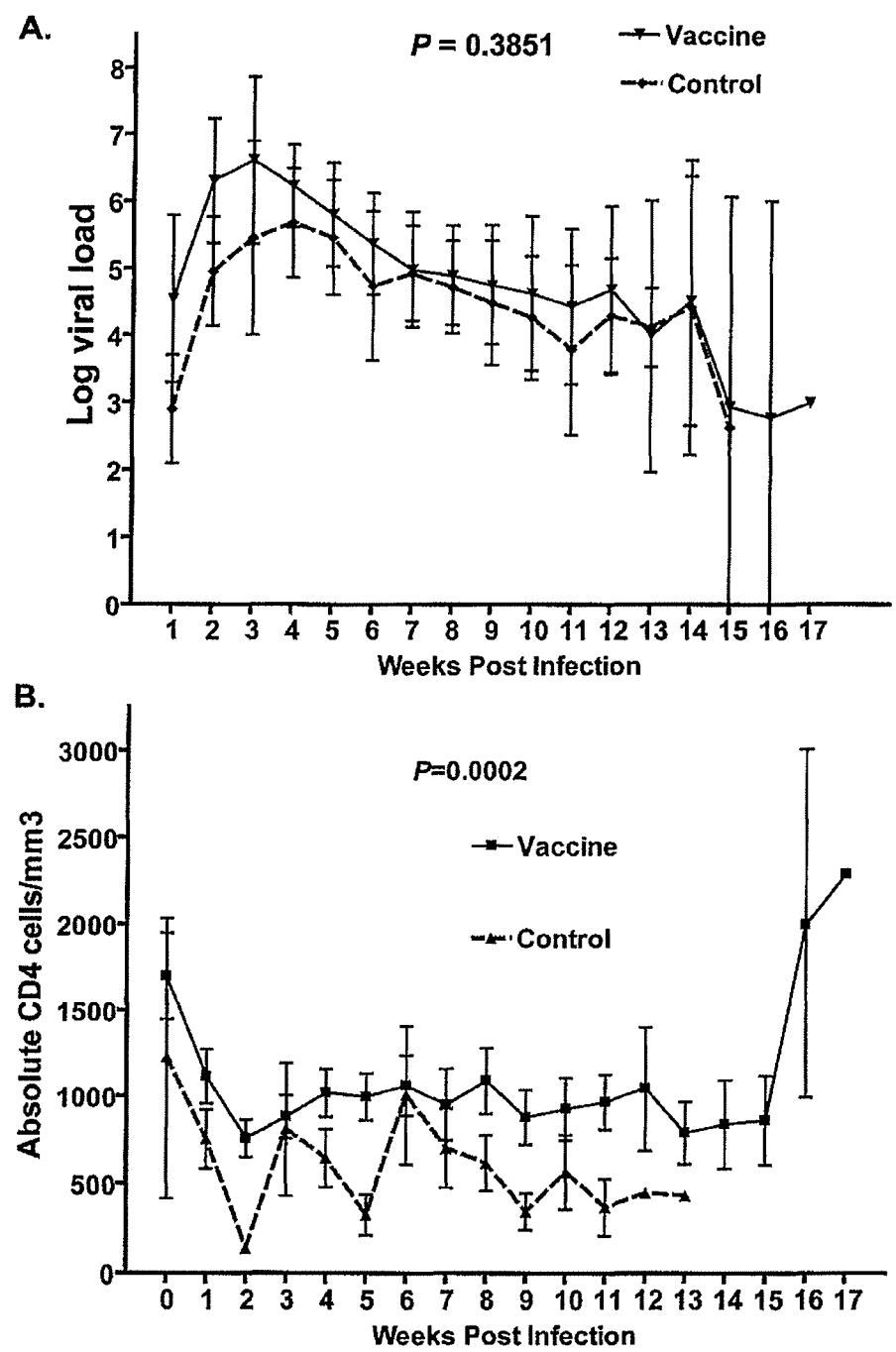
FIG. 11. The viral load and CD4+ T cell counts comparison. The vaccinated macaques maintains significantly higher CD4+ T cell counts than the control group, despite similar or higher viral load due to higher challenge dosage. The results suggested that immune responses to the PCS-peptides may induce many non-infectious viruses that failed to infect CD4+ T cells. A. Mean viral load comparison between vaccinated group and the control group. B. Mean CD4+ T cell counts comparison between vaccinated group and the control group.

These results are shown in FIGS. 7 to 12. The rationale for the vaccine targeting the protease cleavage site is: 1) the sequences at these sites are relatively more conserved than other part of the virus, so HIV is less likely to escape from immune recognition and the infected cells can be destroyed by CD8+ T cells; and 2) the immune response to the virus can drive the virus to mutate to escape immune recognition. However, when the virus mutates, the mutation will make the viral protease unable to cleave the viral polyprotein to produce infectious virions because producing an infectious HIV virus requires all 12 sites be cleaved properly. Specifically, if even one site is not cleaved properly, the virus will not be infectious. This is shown in FIG. 11, which shows that although the macaques in the vaccinated group received much higher dosage of SIVmac239 challenge and their peak viral load is one log higher, their viral load declines faster and they maintain higher CD4+ T cell counts. This data suggests that the virus in the vaccinated group are not vary infectious. Thus, this experiment confirmed the two rationale for this vaccine approach. The $3^{rd}$ rationale is that the focused immune response can avoid generating unnecessary immune response that will activate more CD4+ T cells and recruit more viral target cells to the infection site and help HIV virus to establish infection. This vaccine approach induces viral mutation and escape to the disadvantage of the virus.

Figure 7:
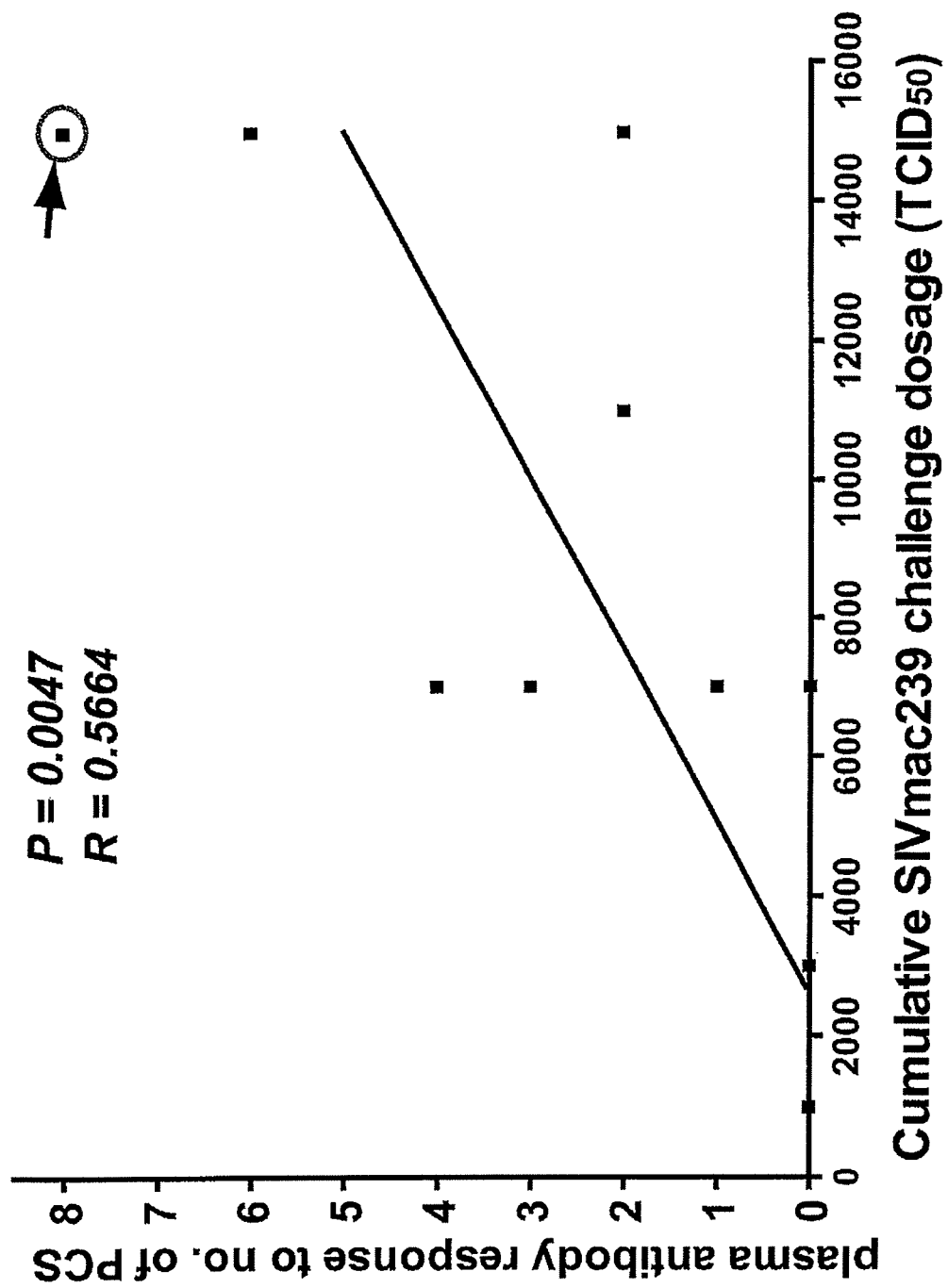
FIG. 7. Macaques with plasma antibody to peptides overlapping the protease cleavage sites are better protected from higher dosage of intrarectal SIVmac239 challenge. A macaque with antibody to 8 different PCS sites is not infected (indicated by arrow and circled).
Figure 8:
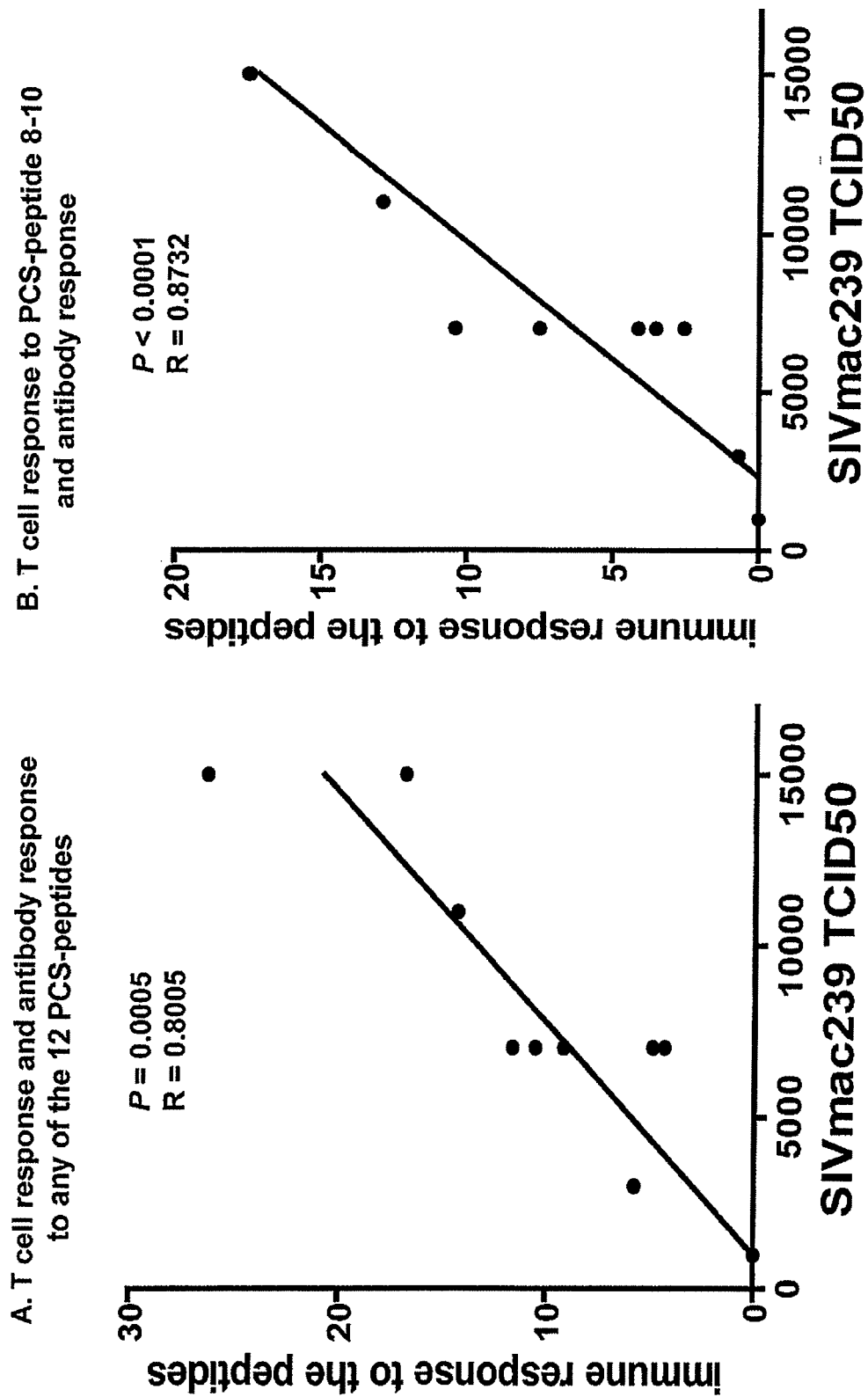
FIG. 8. Macaques with antibody and T cell responses to the peptides overlapping the 12 protease cleavage sites are protected against higher cumulative SIVmac239 challenge. Macaques with antibody and T cell responses to more of the peptides are better protected.

Because of the diversity and heterogeneity of MHC class I and II of Cynomolgus macaques, not all macaques can generate antibody or T cell responses to the peptides overlapping the 12 protease cleavage sites and there is considerable variation in antibody and T cell responses to the PCS-peptides among macaques immunized with the rVSV-PCS and boosted with nanopackaged peptides. The vaccine results showed that antibody responses to the peptides overlapping the 12 protease cleavage sites correlate with protection against higher cumulative dosage of SIVmac239 intrarectal challenge (FIG. 7). Macaques with both T cell and antibody responses to the PCS-peptides are better protected (FIG. 8).

FIG. 9 on the right shows the survival analysis of SIVmac239 intrarectal challenge and the odds ratio of protection for macaques with good T cell and antibody responses to the peptides overlapping the protease cleavage sites.

Figure 12:
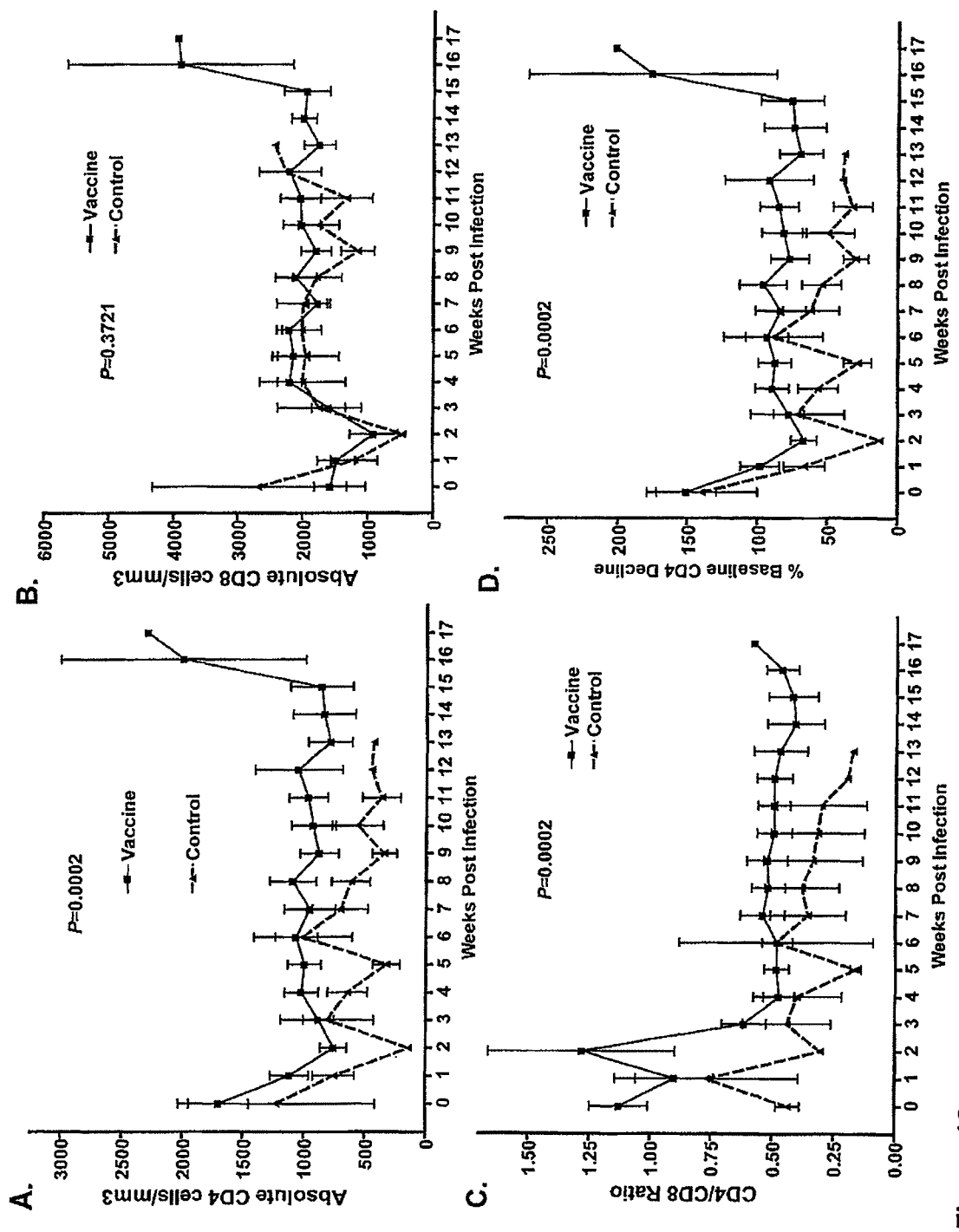
FIG. 12. Comparison of absolute CD4+ T cell counts, absolute CD8+ T cell counts, CD4/CD8 T cell ratio and the % of baseline CD4 decline between the macaques in the vaccinated group and the macaques in the control group. A. Absolute CD4+ T cell counts comparison. B. Absolute CD8+ T cell counts comparison. C. CD4/CD& T cell ratio comparison. D. % Baseline CD4 decline comparison. Red lines represent the control group. Black lines represent the vaccinated group.

We monitored viral load and conducted whole blood $CD4^+$ and $CD8^+$ T cell counts after the macaques have been infected. Since the vaccinated macaques have been challenged with higher dosage of SIVmac239, the comparison of the peak viral load is not fair. It appears that despite the higher peak viral load in the vaccinated macaques due to the higher challenge dosage, their viral load declines much faster than the control group (FIG. 10). Furthermore, the vaccinated macaques maintain significantly higher CD4+ T cell counts than the control group and maintain a significantly higher CD4+/CD8+ ratio (FIGS. 11 and 12) whereas there is no significant difference in CD8+ T cell counts between vaccinated macaques and the control group (FIG. 12). These results indicated that immune responses to the PCS-peptides may induce many non-infectious viruses that failed to infect CD4+ T cells.

Furthermore, for this vaccine strategy to work, a given individual must have an HLA class I allele that can recognize one of the epitope/peptide overlapping one of the 12 protease cleavage sites of HIV-1. Every individual has a total of 6 class I alleles from 3 class I genes (HLA-A, HLA-B and HLA-C) and the utility of the vaccine depends on how many individuals in a population have at least one of the HLA class I alleles that can recognize the peptide overlapping one of the 12 protease cleavage sites. For this vaccine strategy to work best, a given individual should also have a HLA class II allele that can recognize one of the epitopes/peptide overlapping one of the 12 protease cleavage sites of HIV-1. Every individual has two DRB1 alleles, two DQA1/DQB1 allele pairs and two DPA1/DPB1 allele pairs. The utility of this vaccine approach also depends on how many individuals in a population who have at least one of these class II allele/allele pairs that can recognize the peptide overlapping one of the 12 protease cleavage sites.

Figure 13B:
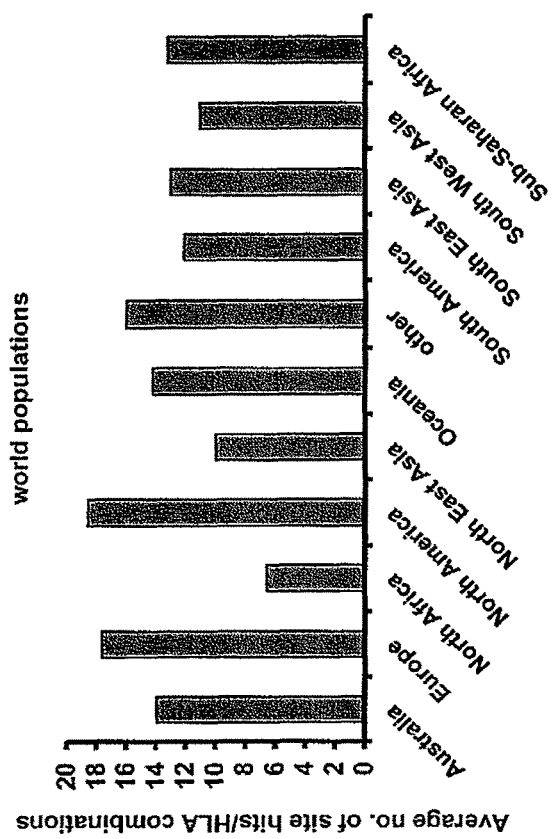
FIG. 13b. Population coverage analysis of epitope hits in the number of protease cleavage sites for each HLA combination in the world population. This shows that epitopes of multiple protease cleavage sites can be recognized by individuals in most populations.
Figure 13A:
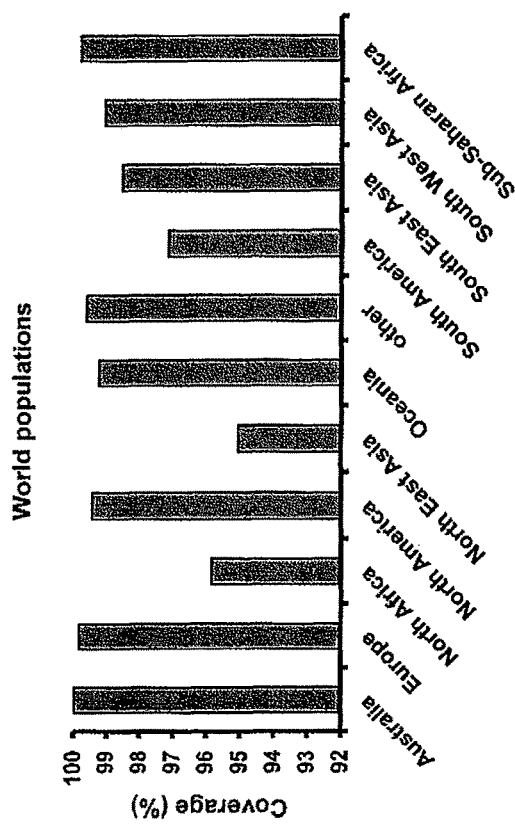
FIG. 13a. Population coverage analysis based on the population HLA class I allele frequencies and their epitopes overlapping the 12 protease cleavage sites. The results showed that this vaccine strategy can be applied to all populations in the world and have greater than 95% coverage.

Consequently, we examined the population coverage using several approaches:

a. We analyzed the currently known HLA class I epitopes overlapping the 12 protease cleavage sites. The percentage of the population that would recognize at least one of the sites is 86% for Caucasian in North America and 62-71.8% for individuals in sub-Saharan Africa.

b. We used computational methods based on the epitope binding motifs of HLA class I alleles and population allele frequencies. Epitope prediction using two different computational algorithms showed that the population coverage is very high (FIG. 13).

c. We screened epitopes of 8 common HLA class I alleles using iTopia Epitope Discovery System and confirmed the epitopes by IFN-gamma ELISPOT assays using patient PBMCs. Screen using iTopia Figure A. Epitope prediction using NetMHCpan (Nielsen et al.) Epitope Discovery System showed that the percentage of individuals recognizing at least one PCS is very high.

The population coverage was predicted using computational algorithms, the Population Coverage Calculator with the Glade A and D peptides overlapping the protease cleavage sites (PCSs). The population coverage was also calculated based on the T cell epitopes that have already been identified at these sites. Furthermore, the peptides overlapping the 12 PCSs were screened with 8 HLA class I alleles using iTopia Epitope Discovery system and confirmed using IFNγ ELISPOT assays with PBMCs.

Analysis using all three approaches showed that the percentage of populations in the world can recognize peptides overlapping at least one PCS is very high, including more than 90% population in Sub-Saharan Africa. iTopia epitope Discovery System screen showed that the eight common HLA alleles have epitopes in multiple PCSs (4 to 12).

The invention claimed is:

1. A method of eliciting an immune reaction in an individual comprising administering to an individual in need of such treatment an effective amount of a nucleic acid molecule encoding an amino acid sequence as set forth in any one of SEQ ID NO: 1-12, said nucleic acid molecule being operably linked to a suitable promoter and being inserted into a suitable expression system.

2. The method according to claim 1 comprising administering to the individual in need of such treatment an effective amount of one or more nucleic acid molecules encoding the amino acid sequences as set forth in SEQ ID NO:1-12.

3. The method according to claim 1 comprising administering to the individual in need of such treatment an effective amount of 12 nucleic acid molecules, each representative one of said nucleic acid molecules encoding the amino acid sequence as set forth in a respective one of SEQ ID NO: 1-12.

4. The method according to claim 1 wherein the expression system is a viral vector.

5. The method according to claim 4 wherein the viral vector is Vesicular Stomatitis Virus (VSV).

* * * * *

SEQUENCE LISTING

```
<160> NUMBER OF SEQ ID NOS: 48

<210> SEQ ID NO 1
<211> LENGTH: 20
<212> TYPE: PRT
<213> ORGANISM: Human immunodeficiency virus

<400> SEQUENCE: 1

Gly Asn Ser Ser Lys Val Ser Gln Asn Tyr Pro Ile Val Gln Asn Leu
1               5                   10                  15

Gln Gly Gln Met
```

-continued

20

<210> SEQ ID NO 2
<211> LENGTH: 20
<212> TYPE: PRT
<213> ORGANISM: Human immunodeficiency virus

<400> SEQUENCE: 2

Gly Gly Pro Ser His Lys Ala Arg Val Leu Ala Glu Ala Met Ser Gln
1               5                   10                  15

Val Thr Asn Thr
            20

<210> SEQ ID NO 3
<211> LENGTH: 20
<212> TYPE: PRT
<213> ORGANISM: Human immunodeficiency virus

<400> SEQUENCE: 3

Met Ser Gln Val Gln His Thr Asn Ile Met Met Gln Arg Gly Asn Phe
1               5                   10                  15

Lys Gly Gln Lys
            20

<210> SEQ ID NO 4
<211> LENGTH: 20
<212> TYPE: PRT
<213> ORGANISM: Human immunodeficiency virus

<400> SEQUENCE: 4

Met Lys Asp Cys Thr Glu Arg Gln Ala Asn Phe Leu Gly Lys Ile Trp
1               5                   10                  15

Pro Ser Asn Lys
            20

<210> SEQ ID NO 5
<211> LENGTH: 20
<212> TYPE: PRT
<213> ORGANISM: Human immunodeficiency virus

<400> SEQUENCE: 5

Pro Ser His Lys Gly Arg Pro Gly Asn Phe Leu Gln Ser Arg Pro Glu
1               5                   10                  15

Pro Thr Ala Pro
            20

<210> SEQ ID NO 6
<211> LENGTH: 20
<212> TYPE: PRT
<213> ORGANISM: Human immunodeficiency virus

<400> SEQUENCE: 6

Met Lys Asp Cys Thr Glu Arg Gln Ala Asn Phe Leu Arg Glu Asn Leu
1               5                   10                  15

Ala Phe Gln Gln
            20

<210> SEQ ID NO 7
<211> LENGTH: 20
<212> TYPE: PRT
<213> ORGANISM: Human immunodeficiency virus

<400> SEQUENCE: 7

Ala Asn Phe Leu Arg Glu Asn Leu Ala Phe Gln Gln Gly Glu Ala Arg
1               5                   10                  15

Glu Phe Ser Ser
            20

<210> SEQ ID NO 8
<211> LENGTH: 20
<212> TYPE: PRT
<213> ORGANISM: Human immunodeficiency virus

<400> SEQUENCE: 8

Glu Arg Gln Gly Thr Val Ser Phe Ser Phe Pro Gln Ile Thr Leu Trp
1               5                   10                  15

Gln Arg Pro Leu
            20

<210> SEQ ID NO 9
<211> LENGTH: 20
<212> TYPE: PRT
<213> ORGANISM: Human immunodeficiency virus

<400> SEQUENCE: 9

Leu Thr Gln Ile Gly Cys Thr Leu Asn Phe Pro Ile Ser Pro Ile Glu
1               5                   10                  15

Thr Val Pro Val
            20

<210> SEQ ID NO 10
<211> LENGTH: 20
<212> TYPE: PRT
<213> ORGANISM: Human immunodeficiency virus
<220> FEATURE:
<221> NAME/KEY: VARIANT
<222> LOCATION: (5)..(5)
<223> OTHER INFORMATION: A or I

<400> SEQUENCE: 10

Lys Glu Pro Ile Xaa Gly Ala Glu Thr Phe Tyr Val Asp Gly Ala Ala
1               5                   10                  15

Asn Arg Glu Thr
            20

<210> SEQ ID NO 11
<211> LENGTH: 20
<212> TYPE: PRT
<213> ORGANISM: Human immunodeficiency virus

<400> SEQUENCE: 11

Leu Val Ser Asn Gly Ile Arg Lys Val Leu Phe Leu Asp Gly Ile Asp
1               5                   10                  15

Lys Ala Gln Glu
            20

<210> SEQ ID NO 12
<211> LENGTH: 20
<212> TYPE: PRT
<213> ORGANISM: Human immunodeficiency virus

<400> SEQUENCE: 12

Thr Ala Gln Thr Asn Pro Asp Cys Ala Trp Leu Glu Ala Gln Glu Glu
1               5                   10                  15

Glu Glu Val Gly

<210> SEQ ID NO 13
<211> LENGTH: 60
<212> TYPE: DNA
<213> ORGANISM: Human immunodeficiency virus

<400> SEQUENCE: 13
ggcaacagca gcaaggtgag ccagaactac cccatcgtgc agaacctgca gggccagatg    60

<210> SEQ ID NO 14
<211> LENGTH: 60
<212> TYPE: DNA
<213> ORGANISM: Human immunodeficiency virus

<400> SEQUENCE: 14
ggcggcccca gccacaaggc cagggtgctg gccgaggcca tgagccaggt gaccaacacc    60

<210> SEQ ID NO 15
<211> LENGTH: 60
<212> TYPE: DNA
<213> ORGANISM: Human immunodeficiency virus

<400> SEQUENCE: 15
atgagccagg tgcagcacac caacatcatg atgcagaggg gcaacttcaa gggccagaag    60

<210> SEQ ID NO 16
<211> LENGTH: 60
<212> TYPE: DNA
<213> ORGANISM: Human immunodeficiency virus

<400> SEQUENCE: 16
atgaaggact gcaccgagag gcaggccaac ttcctgggca agatctggcc cagcaacaag    60

<210> SEQ ID NO 17
<211> LENGTH: 60
<212> TYPE: DNA
<213> ORGANISM: Human immunodeficiency virus

<400> SEQUENCE: 17
cccagccaca agggcaggcc cggcaacttc ctgcagagca ggcccgagcc caccgccccc    60

<210> SEQ ID NO 18
<211> LENGTH: 60
<212> TYPE: DNA
<213> ORGANISM: Human immunodeficiency virus

<400> SEQUENCE: 18
atgaaggact gcaccgagag gcaggccaac ttcctgaggg agaacctggc cttccagcag    60

<210> SEQ ID NO 19
<211> LENGTH: 60
<212> TYPE: DNA
<213> ORGANISM: Human immunodeficiency virus

<400> SEQUENCE: 19
gccaacttcc tgagggagaa cctggccttc cagcagggcg aggccaggga gttcagcagc    60

<210> SEQ ID NO 20
<211> LENGTH: 60
<212> TYPE: DNA
<213> ORGANISM: Human immunodeficiency virus

<400> SEQUENCE: 20
gagaggcagg gcaccgtgag cttcagcttc ccccagatca ccctgtggca gaggcccctg    60

<210> SEQ ID NO 21
<211> LENGTH: 60
<212> TYPE: DNA
<213> ORGANISM: Human immunodeficiency virus

<400> SEQUENCE: 21
ctgacccaga tcggctgcac cctgaacttc cccatcagcc ccatcgagac cgtgcccgtg    60

<210> SEQ ID NO 22
<211> LENGTH: 60
<212> TYPE: DNA
<213> ORGANISM: Human immunodeficiency virus

<400> SEQUENCE: 22
aaggagccca tcrycggcgc cgagaccttc tacgtggacg gcgccgccaa cagggagacc    60

<210> SEQ ID NO 23
<211> LENGTH: 60
<212> TYPE: DNA
<213> ORGANISM: Human immunodeficiency virus

<400> SEQUENCE: 23
ctggtgagca acggcatcag gaaggtgctg ttcctggacg gcatcgacaa ggcccaggag    60

<210> SEQ ID NO 24
<211> LENGTH: 60
<212> TYPE: DNA
<213> ORGANISM: Human immunodeficiency virus

<400> SEQUENCE: 24
accgcccaga ccaaccccga ctgcgcctgg ctggaggccc aggaggagga ggaggtgggc    60

<210> SEQ ID NO 25
<211> LENGTH: 20
<212> TYPE: PRT
<213> ORGANISM: Simian immunodeficiency virus

<400> SEQUENCE: 25

Ala Pro Ser Ser Gly Arg Gly Gly Asn Tyr Pro Val Gln Gln Ile Gly
1               5                   10                  15

Gly Asn Tyr Val
            20

<210> SEQ ID NO 26
<211> LENGTH: 20
<212> TYPE: PRT
<213> ORGANISM: Simian immunodeficiency virus

<400> SEQUENCE: 26

Gly Gly Pro Gly Gln Lys Ala Arg Leu Met Ala Glu Ala Leu Lys Glu
1               5                   10                  15

Ala Leu Ala Pro
            20

<210> SEQ ID NO 27
<211> LENGTH: 20
<212> TYPE: PRT
<213> ORGANISM: Simian immunodeficiency virus

<400> SEQUENCE: 27

```
Leu Ala Pro Val Pro Ile Pro Phe Ala Ala Ala Gln Gln Arg Gly Pro
1               5                   10                  15

Arg Lys Pro Ile
            20

<210> SEQ ID NO 28
<211> LENGTH: 20
<212> TYPE: PRT
<213> ORGANISM: Simian immunodeficiency virus

<400> SEQUENCE: 28

Met Ala Lys Cys Pro Asp Arg Gln Ala Gly Phe Leu Gly Leu Gly Pro
1               5                   10                  15

Trp Gly Lys Lys
            20

<210> SEQ ID NO 29
<211> LENGTH: 20
<212> TYPE: PRT
<213> ORGANISM: Simian immunodeficiency virus

<400> SEQUENCE: 29

Gly Pro Trp Gly Lys Lys Pro Arg Asn Phe Pro Met Ala Gln Val His
1               5                   10                  15

Gln Gly Leu Met
            20

<210> SEQ ID NO 30
<211> LENGTH: 20
<212> TYPE: PRT
<213> ORGANISM: Simian immunodeficiency virus

<400> SEQUENCE: 30

Tyr Gly Gln Met Pro Arg Gln Thr Gly Gly Phe Phe Arg Pro Trp Ser
1               5                   10                  15

Met Gly Lys Glu
            20

<210> SEQ ID NO 31
<211> LENGTH: 20
<212> TYPE: PRT
<213> ORGANISM: Simian immunodeficiency virus

<400> SEQUENCE: 31

Trp Ser Met Gly Lys Glu Ala Pro Gln Phe Pro His Gly Ser Ser Ala
1               5                   10                  15

Ser Gly Ala Asp
            20

<210> SEQ ID NO 32
<211> LENGTH: 20
<212> TYPE: PRT
<213> ORGANISM: Simian immunodeficiency virus

<400> SEQUENCE: 32

Leu Gln Gly Gly Asp Arg Gly Phe Ala Ala Pro Gln Phe Ser Leu Trp
1               5                   10                  15

Arg Arg Pro Val
            20

<210> SEQ ID NO 33
<211> LENGTH: 20
```

```
<212> TYPE: PRT
<213> ORGANISM: Simian immunodeficiency virus

<400> SEQUENCE: 33

Leu Thr Ala Leu Gly Met Ser Leu Asn Phe Pro Ile Ala Lys Val Glu
1               5                   10                  15

Pro Val Lys Val
            20

<210> SEQ ID NO 34
<211> LENGTH: 20
<212> TYPE: PRT
<213> ORGANISM: Simian immunodeficiency virus

<400> SEQUENCE: 34

Lys Asp Pro Ile Glu Gly Glu Glu Thr Tyr Tyr Thr Asp Gly Ser Cys
1               5                   10                  15

Asn Lys Gln Ser
            20

<210> SEQ ID NO 35
<211> LENGTH: 20
<212> TYPE: PRT
<213> ORGANISM: Simian immunodeficiency virus

<400> SEQUENCE: 35

Leu Val Ser Gln Gly Ile Arg Gln Val Leu Phe Leu Glu Lys Ile Glu
1               5                   10                  15

Pro Ala Gln Glu
            20

<210> SEQ ID NO 36
<211> LENGTH: 20
<212> TYPE: PRT
<213> ORGANISM: Simian immunodeficiency virus

<400> SEQUENCE: 36

Asn Gln Gly Gln Tyr Met Asn Thr Pro Trp Arg Asn Pro Ala Glu Glu
1               5                   10                  15

Arg Glu Lys Leu
            20

<210> SEQ ID NO 37
<211> LENGTH: 60
<212> TYPE: DNA
<213> ORGANISM: Simian immunodeficiency virus

<400> SEQUENCE: 37
gcaccatcta gcggcagagg aggaaattac ccagtacaac aaataggtgg taactatgtc    60

<210> SEQ ID NO 38
<211> LENGTH: 60
<212> TYPE: DNA
<213> ORGANISM: Simian immunodeficiency virus

<400> SEQUENCE: 38 gggggggccgg gacagaaggc tagattaatg gcagaagccc tgaaagaggc cctcgcacca    60

<210> SEQ ID NO 39
<211> LENGTH: 60
<212> TYPE: DNA
<213> ORGANISM: Simian immunodeficiency virus
```

<400> SEQUENCE: 39
ctcgcaccag tgccaatccc ttttgcagca gcccaacaga ggggaccaag aaagccaatt    60

<210> SEQ ID NO 40
<211> LENGTH: 60
<212> TYPE: DNA
<213> ORGANISM: Simian immunodeficiency virus

<400> SEQUENCE: 40
atggccaaat gcccagacag acaggcgggt tttttaggcc ttggtccatg gggaagaag    60

<210> SEQ ID NO 41
<211> LENGTH: 60
<212> TYPE: DNA
<213> ORGANISM: Simian immunodeficiency virus

<400> SEQUENCE: 41
ggtccatggg aaagaagcc ccgcaatttc cccatggctc aagtgcatca ggggctgatg    60

<210> SEQ ID NO 42
<211> LENGTH: 60
<212> TYPE: DNA
<213> ORGANISM: Simian immunodeficiency virus

<400> SEQUENCE: 42
tatggccaaa tgcccagaca gacaggcggg ttttttaggc cttggtccat ggggaagaa    60

<210> SEQ ID NO 43
<211> LENGTH: 60
<212> TYPE: DNA
<213> ORGANISM: Simian immunodeficiency virus

<400> SEQUENCE: 43
tggtccatgg ggaaagaagc ccgcaatttt ccccatggct caagtgcatc aggggctgat    60

<210> SEQ ID NO 44
<211> LENGTH: 60
<212> TYPE: DNA
<213> ORGANISM: Simian immunodeficiency virus

<400> SEQUENCE: 44
ttacaaggag gtgacagagg atttgctgca cctcaattct ctctttggag gagaccagta    60

<210> SEQ ID NO 45
<211> LENGTH: 60
<212> TYPE: DNA
<213> ORGANISM: Simian immunodeficiency virus

<400> SEQUENCE: 45
ctaacagctc tggggatgtc tctaaatttt cccatagcta agtagagcc tgtaaaagtc    60

<210> SEQ ID NO 46
<211> LENGTH: 60
<212> TYPE: DNA
<213> ORGANISM: Simian immunodeficiency virus

<400> SEQUENCE: 46
aaggacccta tagagggaga agaaacctat tatacagatg gatcatgtaa taaacagtca    60

<210> SEQ ID NO 47
<211> LENGTH: 60
<212> TYPE: DNA
<213> ORGANISM: Simian immunodeficiency virus

```
<400> SEQUENCE: 47
ctagttagtc aagggattag acaagttctc ttcttggaaa agatagagcc agcacaagaa      60

<210> SEQ ID NO 48
<211> LENGTH: 60
<212> TYPE: DNA
<213> ORGANISM: Simian immunodeficiency virus

<400> SEQUENCE: 48
aatcagggac agtatatgaa tactccatgg agaaacccag ctgaagagag agaaaaatta      60
```